US008697656B2

(12) United States Patent
Fournial et al.

(10) Patent No.: US 8,697,656 B2
(45) Date of Patent: Apr. 15, 2014

(54) COMPOUNDS, IN PARTICULAR PEPTIDES, COMPOSITIONS COMPRISING THEM AND COSMETIC AND DERMO-PHARMACEUTICAL USES

(75) Inventors: Arnaud Fournial, Paris (FR); Philippe Mondon, Cachan (FR); Olivier Peschard, Saint-Prest (FR)

(73) Assignee: SEDERMA (FR)

( * ) Notice: Subject to any disclaimer, the term of this patent is extended or adjusted under 35 U.S.C. 154(b) by 0 days.

(21) Appl. No.: 13/144,614

(22) PCT Filed: Jan. 15, 2010

(86) PCT No.: PCT/IB2010/050190
§ 371 (c)(1),
(2), (4) Date: Jul. 14, 2011

(87) PCT Pub. No.: WO2010/082175
PCT Pub. Date: Jul. 22, 2010

(65) Prior Publication Data
US 2012/0014887 A1 Jan. 19, 2012

(30) Foreign Application Priority Data
Jan. 16, 2009 (FR) ..................... 09 50249

(51) Int. Cl.
*A61K 38/06* (2006.01)
*A61Q 19/00* (2006.01)
*C07K 5/09* (2006.01)
*A61Q 19/08* (2006.01)

(52) U.S. Cl.
CPC .............. *A61K 38/06* (2013.01); *A61Q 19/08* (2013.01); *C07K 5/0815* (2013.01)
USPC .......... 514/21.9; 530/331; 514/18.6; 514/18.8

(58) Field of Classification Search
CPC ....... A61K 8/64; A61K 38/06; C07K 5/0815; A61Q 1/06; A61Q 7/00; A61Q 19/00; A61Q 19/02; A61Q 19/06; A61Q 19/08; A61Q 5/006
See application file for complete search history.

(56) References Cited

U.S. PATENT DOCUMENTS

| | | | |
|---|---|---|---|
| 1,985,424 A | 12/1934 | Piggott | |
| 2,396,278 A | 3/1946 | Lind | |
| 2,438,091 A | 3/1948 | Lynch | |
| 2,486,921 A | 11/1949 | Byerly | |
| 2,486,922 A | 11/1949 | Strain | |
| 2,528,378 A | 10/1950 | Mannheimer | |
| 2,658,072 A | 11/1953 | Schwartz | |
| 2,703,798 A | 3/1955 | Schwartz | |
| 2,798,053 A | 7/1957 | Brown | |
| 2,809,971 A | 10/1957 | Bernstein | |
| 2,826,551 A | 3/1958 | Geen | |
| 2,965,576 A | 12/1960 | Wilson | |
| 3,155,591 A | 11/1964 | Hilfer | |
| 3,236,733 A | 2/1966 | Karsten et al. | |
| 3,311,624 A | 3/1967 | Ohnacker et al. | |
| 3,332,880 A | 7/1967 | Kesller et al. | |
| 3,755,560 A | 8/1973 | Dickert | |
| 3,761,418 A | 9/1973 | Parran, Jr. et al. | |
| 3,929,678 A | 12/1975 | Laughlin et al. | |
| 3,958,581 A | 5/1976 | Abegg et al. | |
| 3,959,461 A | 5/1976 | Bailey et al. | |
| 3,962,418 A | 6/1976 | Birkofer | |
| 3,964,500 A | 6/1976 | Drakoff | |
| 4,152,416 A | 5/1979 | Spitzer et al. | |
| 4,202,879 A | 5/1980 | Shelton | |
| 4,323,683 A | 4/1982 | Bolich, Jr. et al. | |
| 4,345,080 A | 8/1982 | Bolich, Jr. | |
| 4,364,837 A | 12/1982 | Pader | |
| 4,379,753 A | 4/1983 | Bolich, Jr. | |
| 4,387,090 A | 6/1983 | Bolich, Jr. | |
| 4,421,769 A | 12/1983 | Dixon et al. | |
| 4,470,982 A | 9/1984 | Winkler | |
| 4,509,949 A | 4/1985 | Huang et al. | |
| 4,557,853 A | 12/1985 | Collins | |
| 4,599,379 A | 7/1986 | Flesher et al. | |
| 4,628,078 A | 12/1986 | Glover et al. | |

(Continued)

FOREIGN PATENT DOCUMENTS

| | | | |
|---|---|---|---|
| EP | 2 288 68 A2 | 7/1987 | |
| EP | 330369 A1 | 8/1989 | |

(Continued)

OTHER PUBLICATIONS

Brosnan et al, The Sulfur-Containing Amino Acids: An Overview, J. Nutr., 2006, 136, pp. 1636S-1640S.*
Baurin et al, Preliminary screening of some tropical plants for anti-tyrosinase activity, Journal of Ethnopharmacology, 2002, 82, pp. 155-158.*
KR 2002/0016960 A, filed with IDS, Machine translation used and enclosed, pp. 1-10.*
Herouy et al.; Eur. J. Dermatology, Apr.-May 2000, 10:3, pp. 173-180.
Woessner, J.F.; Faseb J., 1991, vol. 5, pp. 2145-2154.
International Search Report for PCT/IB2010/050190 dated Aug. 30, 2010.

*Primary Examiner* — Julie Ha
*Assistant Examiner* — Li Ni Komatsu
(74) *Attorney, Agent, or Firm* — Lerner, David, Littenberg, Krumholz & Mentlik, LLP

(57) ABSTRACT

The present invention concerns a peptide of following formula I: R being a side chain having at least one heteroatom selected from sulfur, nitrogen and oxygen in a carbonyl form (C=O); $R_1$ being either H or a lipophilic chain; $R^2$ being either OH or a lipophilic chain. More particularly the present invention concerns a cosmetic composition comprising a peptide as recited above and a physiologically acceptable medium. Results on the activity of the compounds are obtained and on the general state of the skin and its appendages, in particular via the stimulation of extracellular matrix components.

15 Claims, No Drawings

(56) References Cited

U.S. PATENT DOCUMENTS

| | | |
|---|---|---|
| 4,741,855 A | 5/1988 | Grote et al. |
| 4,800,197 A | 1/1989 | Kowcz et al. |
| 4,816,261 A | 3/1989 | Luebbe et al. |
| 4,835,206 A | 5/1989 | Farrar et al. |
| 4,847,071 A | 7/1989 | Bissett et al. |
| 4,849,484 A | 7/1989 | Heard |
| 4,885,311 A | 12/1989 | Parish et al. |
| 4,960,764 A | 10/1990 | Figueroa, Jr. et al. |
| 4,970,252 A | 11/1990 | Sakuta et al. |
| 4,976,953 A | 12/1990 | Orr et al. |
| 5,011,681 A | 4/1991 | Ciotti et al. |
| 5,049,584 A | 9/1991 | Purcell et al. |
| 5,073,371 A | 12/1991 | Turner et al. |
| 5,073,372 A | 12/1991 | Turner et al. |
| 5,087,445 A | 2/1992 | Haffey et al. |
| 5,100,660 A | 3/1992 | Hawe et al. |
| 5,104,646 A | 4/1992 | Bolich, Jr. et al. |
| 5,106,609 A | 4/1992 | Bolich, Jr. et al. |
| 5,120,532 A | 6/1992 | Wells et al. |
| 5,124,356 A | 6/1992 | Purcell et al. |
| RE34,075 E | 9/1992 | Purcell et al. |
| 5,151,209 A | 9/1992 | McCall et al. |
| 5,151,210 A | 9/1992 | Steuri et al. |
| RE34,584 E | 4/1994 | Grote et al. |
| 5,412,004 A | 5/1995 | Tachibana et al. |
| 5,487,884 A | 1/1996 | Bissett et al. |
| 5,607,980 A | 3/1997 | McAtee et al. |
| 5,652,228 A | 7/1997 | Bissett |
| 5,654,362 A | 8/1997 | Schulz, Jr. et al. |
| 5,681,852 A | 10/1997 | Bissett |
| 5,686,082 A | 11/1997 | N'Guyen |
| 5,736,537 A | 4/1998 | Gubernick et al. |
| 5,760,116 A | 6/1998 | Kilgour et al. |
| 5,811,487 A | 9/1998 | Schulz, Jr. et al. |
| 5,837,793 A | 11/1998 | Harashima et al. |
| 5,939,082 A | 8/1999 | Oblong et al. |
| 6,068,834 A | 5/2000 | Kvalnes et al. |
| 6,159,485 A | 12/2000 | Yu et al. |
| 6,190,645 B1 | 2/2001 | SaNogueira et al. |
| 6,372,717 B1 | 4/2002 | Greff |
| 6,620,419 B1 | 9/2003 | Lintner |
| 2004/0120918 A1 | 6/2004 | Lintner et al. |
| 2004/0132667 A1 | 7/2004 | Lintner |
| 2007/0099842 A1* | 5/2007 | Ziegler et al. ............ 514/18 |

FOREIGN PATENT DOCUMENTS

| | | |
|---|---|---|
| EP | 0518772 A1 | 12/1992 |
| EP | 0518773 A1 | 12/1992 |
| EP | 1722864 A1 | 11/2006 |
| FR | 00/03846 M | 12/1964 |
| FR | 2654619 A1 | 5/1991 |
| FR | 2694195 A1 | 2/1994 |
| FR | 2702766 A1 | 9/1994 |
| FR | 2 732 215 A1 | 10/1996 |
| FR | 2733149 A1 | 10/1996 |
| FR | 2771002 A1 | 5/1999 |
| FR | 2781231 A1 | 1/2000 |
| FR | 2788058 A1 | 7/2000 |
| FR | 2810323 A1 | 12/2001 |
| FR | 2854897 A1 | 11/2004 |
| GB | 849 433 A | 9/1960 |
| GB | 2 274 585 A | 8/1994 |
| KR | 20020016960 A | 3/2002 |
| WO | 91/16034 A1 | 10/1991 |
| WO | 91/16035 A1 | 10/1991 |
| WO | 93/23028 A1 | 11/1993 |
| WO | 95/34280 A1 | 12/1995 |
| WO | 96/33689 A1 | 10/1996 |
| WO | 97/05856 A1 | 2/1997 |
| WO | 98/05299 A1 | 2/1998 |
| WO | 98/07744 A1 | 2/1998 |
| WO | 98/43607 A1 | 10/1998 |
| WO | 99/12968 A2 | 3/1999 |
| WO | 99/18927 A1 | 4/1999 |
| WO | 99/25369 A1 | 5/1999 |
| WO | 9940897 A1 | 8/1999 |
| WO | 00/15188 A1 | 3/2000 |
| WO | 00/40611 A1 | 7/2000 |
| WO | 00/42071 A2 | 7/2000 |
| WO | 00/43417 A1 | 7/2000 |
| WO | 00/58347 A1 | 10/2000 |
| WO | 01/43701 A2 | 6/2001 |
| WO | 01/64178 A1 | 9/2001 |
| WO | 02/15871 A1 | 2/2002 |
| WO | 02076423 | 10/2002 |
| WO | 03017966 A2 | 3/2003 |
| WO | 03/028692 A2 | 4/2003 |
| WO | 03/068141 A2 | 8/2003 |
| WO | 2004/024695 A1 | 3/2004 |
| WO | 2004/099237 A1 | 11/2004 |
| WO | 2006/018652 A2 | 2/2006 |
| WO | 2007/093839 A1 | 8/2007 |
| WO | 2008/093060 A2 | 8/2008 |
| WO | 2010/082176 A2 | 7/2010 |
| WO | 2010/082177 A2 | 7/2010 |

* cited by examiner

SEQUENCE LISTING

<160> NUMBER OF SEQ ID NOS: 37

<210> SEQ ID NO 1
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE

```
<222> LOCATION: (2)..(3)
<223> OTHER INFORMATION: the sulfur of the methionine being di-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 1

Lys Met Met Lys
1

<210> SEQ ID NO 2
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (2)..(2)
<223> OTHER INFORMATION: the sulfur of the methionine being di-
      oxygenated
<220> FEATURE:
<221> NAME/KEY: MISC_FEATURE
<222> LOCATION: (3)..(3)
<223> OTHER INFORMATION: Xaa being the 5-amino-valeric acid (Ava)
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 2

Lys Met Xaa Lys
1

<210> SEQ ID NO 3
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (2)..(2)
<223> OTHER INFORMATION: Xaa being the 5-amino-valeric acid (Ava)
<220> FEATURE:
<221> NAME/KEY: MISC_FEATURE
<222> LOCATION: (3)..(3)
<223> OTHER INFORMATION: the sulfur of the methionine being di-
      oxygenated
<220> FEATURE:
<221> NAME/KEY: MISC_FEATURE
<222> LOCATION: (4)..(4)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
```

```
-continued

<400> SEQUENCE: 3

Lys Xaa Met Lys
1

<210> SEQ ID NO 4
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (1)..(1)
<223> OTHER INFORMATION: the sulfur of the methionine being di-
      oxygenated
<220> FEATURE:
<221> NAME/KEY: MISC_FEATURE
<222> LOCATION: (3)..(3)
<223> OTHER INFORMATION: Xaa being the 5-amino-valeric acid (Ava)
<220> FEATURE:
<221> NAME/KEY: MISC_FEATURE
<222> LOCATION: (4)..(4)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain

<400> SEQUENCE: 4

Met Lys Xaa Lys
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 5

Lys Thr Phe Lys
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
```

-continued

```
<222> LOCATION: (2)..(2)
<223> OTHER INFORMATION: The sulfur of the methionine being di-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 6

Lys Met Phe Lys
1

<210> SEQ ID NO 7
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (3)..(3)
<223> OTHER INFORMATION: The sulfur of the methionine being di-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 7

Lys Thr Met Lys
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain
<220> FEATURE:
<221> NAME/KEY: MISC_FEATURE
<222> LOCATION: (4)..(4)
<223> OTHER INFORMATION: The sulfur of the methionine being di-
      oxygenated

<400> SEQUENCE: 8

Lys Thr Phe Met
1

<210> SEQ ID NO 9
```

```
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (1)..(1)
<223> OTHER INFORMATION: The sulfur of the methionine being di-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 9

Met Thr Phe Lys
1

<210> SEQ ID NO 10
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (2)..(2)
<223> OTHER INFORMATION: The sulfur of the methionine being di-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 10

Lys Met Thr Lys
1

<210> SEQ ID NO 11
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (3)..(3)
<223> OTHER INFORMATION: The sulfur of the methionine being di-
      oxygenated
<220> FEATURE:
<221> NAME/KEY: MISC_FEATURE
```

```
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 11

Lys Phe Met Lys
1

<210> SEQ ID NO 12
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (3)..(3)
<223> OTHER INFORMATION: The sulfur of the methionine being di-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 12

Lys Thr Met Phe
1

<210> SEQ ID NO 13
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 13

Gly Gln Pro Arg
1

<210> SEQ ID NO 14
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
```

-continued

```
      aryl, aralkyl, sugar or alkoxy 1 to 24 carbon atom chain
<220> FEATURE:
<221> NAME/KEY: MISC_FEATURE
<222> LOCATION: (2)..(2)
<223> OTHER INFORMATION: The sulfur of the methionine being mono-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 14

Gly Met Pro Arg
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (2)..(2)
<223> OTHER INFORMATION: The sulfur of the methionine being di-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 15

Gly Met Gln Pro
1

<210> SEQ ID NO 16
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (1)..(1)
<223> OTHER INFORMATION: The sulfur of the methionine being di-
      oxygenated
<220> FEATURE:
<221> NAME/KEY: MISC_FEATURE
<222> LOCATION: (4)..(4)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 16

Met Gly His Lys
1
```

```
<210> SEQ ID NO 17
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (1)..(1)
<223> OTHER INFORMATION: The sulfur of the methionine being mono-
      oxygenated
<220> FEATURE:
<221> NAME/KEY: MISC_FEATURE
<222> LOCATION: (5)..(5)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 17

Met Gly Gln Pro Arg
1               5

<210> SEQ ID NO 18
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (5)..(5)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 18

Lys Thr Thr Lys Ser
1               5

<210> SEQ ID NO 19
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (2)..(2)
<223> OTHER INFORMATION: the alcool function of the threonine is
      substituted by a SOCH3 function
<220> FEATURE:
<221> NAME/KEY: MISC_FEATURE
<222> LOCATION: (5)..(5)
<223> OTHER INFORMATION: the OH group can be substituted by an -OR7
``` group or a -NR8R9 group, R7, R8 and R9 being independently from
        each other a hydrogen, an alkyl, aryl, aralkyl, acyl, sulfonyl,
        sugar or alkoxy of 1 to 24 carbon atom chain

<400> SEQUENCE: 19

Lys Thr Thr Lys Ser
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
        sulfonyl group such a biotinoyl group or a group having an alkyl,
        aryl, aralkyl, sugar or alkoxy 1 to 24 carbon atom chain
<220> FEATURE:
<221> NAME/KEY: MISC_FEATURE
<222> LOCATION: (2)..(2)
<223> OTHER INFORMATION: The sulfur of the methionine being di-
        oxygenated
<220> FEATURE:
<221> NAME/KEY: MISC_FEATURE
<222> LOCATION: (5)..(5)
<223> OTHER INFORMATION: the OH group can be substituted by an -OR7
        group or a -NR8R9 group, R7, R8 and R9 being independently from
        each other a hydrogen, an alkyl, aryl, aralkyl, acyl, sulfonyl,
        sugar or alkoxy of 1 to 24 carbon atom chain

<400> SEQUENCE: 20

Lys Met Thr Lys Ser
1               5

<210> SEQ ID NO 21
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
        sulfonyl group such a biotinoyl group or a group having an alkyl,
        aryl, aralkyl, sugar or alkoxy 1 to 24 carbon atom chain
<220> FEATURE:
<221> NAME/KEY: MISC_FEATURE
<222> LOCATION: (1)..(1)
<223> OTHER INFORMATION: The sulfur of the methionine being di-
        oxygenated
<220> FEATURE:
<221> NAME/KEY: MISC_FEATURE
<222> LOCATION: (5)..(5)
<223> OTHER INFORMATION: the OH group can be substituted by an -OR7
        group or a -NR8R9 group, R7, R8 and R9 being independently from
        each other a hydrogen, an alkyl, aryl, aralkyl, acyl, sulfonyl,
        sugar or alkoxy of 1 to 24 carbon atom chain

<400> SEQUENCE: 21

Met Thr Thr Lys Ser
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE -continued

```
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (5)..(5)
<223> OTHER INFORMATION: the serine is alkylated with a CH3  terminal
      and the sulfur atom is di-oxygenated
<220> FEATURE:
<221> NAME/KEY: MISC_FEATURE
<222> LOCATION: (5)..(5)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 22

Lys Thr Thr Lys Ser
1               5

<210> SEQ ID NO 23
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: one of the H may be substituted by an acyl or
      sulfonyl group such a biotinoyl group or a group having an alkyl,
      aryl, aralkyl, sugar or alkoxy 1 to 24 carbon atom chain
<220> FEATURE:
<221> NAME/KEY: MISC_FEATURE
<222> LOCATION: (1)..(1)
<223> OTHER INFORMATION: The sulfur of the methionine being di-
      oxygenated
<220> FEATURE:
<221> NAME/KEY: MISC_FEATURE
<222> LOCATION: (6)..(6)
<223> OTHER INFORMATION: the OH group can be substituted by an -OR7
      group or a -NR8R9 group, R7, R8 and R9 being independently from
      each other a hydrogen, an alkyl, aryl, aralkyl, acyl, sulfonyl,
      sugar or alkoxy of 1 to 24 carbon atom chain

<400> SEQUENCE: 23

Met Lys Thr Thr Lys Ser
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The N terminal can be amidated by a Palmitoyl
      chain

<400> SEQUENCE: 24

Lys Thr Thr Lys Ser
1               5

<210> SEQ ID NO 25
<211> LENGTH: 4
<212> TYPE: PRT
<213> ORGANISM: Artificial sequence
<220> FEATURE:
<223> OTHER INFORMATION: Synthetic peptide

<400> SEQUENCE: 25
```

Arg Ser Arg Lys
1

<210> SEQ ID NO 26
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The N terminal can be amidated by a Palmitoyl
      chain

<400> SEQUENCE: 26

Gly Gln Pro Arg
1

<210> SEQ ID NO 27
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The N terminal can be amidated by a Palmitoyl
      chain

<400> SEQUENCE: 27

Val Gly Val Ala Pro Gly
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (5)..(5)
<223> OTHER INFORMATION: Xaa is either Met or Leu

<400> SEQUENCE: 28

Tyr Gly Gly Phe Xaa
1               5

<210> SEQ ID NO 29
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The sulfur of the methionine being di-
      oxygenated
<220> FEATURE:
<221> NAME/KEY: MISC_FEATURE
<222> LOCATION: (1)..(1)
<223> OTHER INFORMATION: amidation by a Palmitoyl chain on the N
      terminal end

```
<400> SEQUENCE: 29

Met Thr Phe Lys
1

<210> SEQ ID NO 30
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (3)..(3)
<223> OTHER INFORMATION: The sulfur of the methionine being di-
      oxygenated

<400> SEQUENCE: 30

Lys Thr Met Lys
1

<210> SEQ ID NO 31
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (3)..(3)
<223> OTHER INFORMATION: The sulfur of the methionine being di-
      oxygenated

<400> SEQUENCE: 31

Lys Phe Met Lys
1

<210> SEQ ID NO 32
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (4)..(4)
<223> OTHER INFORMATION: The sulfur of the methionine being di-
      oxygenated
<220> FEATURE:
<221> NAME/KEY: MISC_FEATURE
<222> LOCATION: (4)..(4)
<223> OTHER INFORMATION: amidaton with a NH2 group of the C=O terminal

<400> SEQUENCE: 32

Lys Thr Phe Met
1

<210> SEQ ID NO 33
```

```
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (2)..(2)
<223> OTHER INFORMATION: The sulfur of the methionine being di-
      oxygenated

<400> SEQUENCE: 33

Lys Met Thr Lys
1

<210> SEQ ID NO 34
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (2)..(2)
<223> OTHER INFORMATION: The sulfur of the methionine being di-
      oxygenated

<400> SEQUENCE: 34

Lys Met Phe Lys
1

<210> SEQ ID NO 35
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (2)..(2)
<223> OTHER INFORMATION: Xaa being the 5-amino-valeric acid (Ava)
<220> FEATURE:
<221> NAME/KEY: MISC_FEATURE
<222> LOCATION: (3)..(3)
<223> OTHER INFORMATION: The sulfur of the methionine being di-
      oxygenated

<400> SEQUENCE: 35

Lys Xaa Met Lys
1

<210> SEQ ID NO 36
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (2)..(2)
<223> OTHER INFORMATION: The sulfur of the methionine being di-
      oxygenated
<220> FEATURE:
<221> NAME/KEY: MISC_FEATURE
<222> LOCATION: (3)..(3)
<223> OTHER INFORMATION: Xaa being the 5-amino-valeric acid (Ava)

<400> SEQUENCE: 36

Lys Met Xaa Lys
1

<210> SEQ ID NO 37
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: amidation by a Palmitoyl chain on the N
      terminal end

<400> SEQUENCE: 37

Lys Thr Phe Lys
1
```

COMPOUNDS, IN PARTICULAR PEPTIDES, COMPOSITIONS COMPRISING THEM AND COSMETIC AND DERMO-PHARMACEUTICAL USES

CROSS-REFERENCE TO RELATED APPLICATIONS

The present application is a national phase entry under 35 U.S.C. §371 of International Application No. PCT/IB2010/050190, filed Jan. 15, 2010, published in English, which claims benefit of French Patent Application No. 09 50249, filed Jan. 16, 2009. The disclosures of all of said applications are incorporated by reference herein.

TECHNICAL FIELD

The present invention concerns new compounds, in particular peptide compounds, compositions comprising them and uses in the fields of cosmetic, hygiene and personal care products and dermopharmacy.

The present invention concerns the chemical, medical or cosmetics skin and appendages (such as body hair, eyelashes, eyebrow, nails, hairs) care industries for mammals, animals or human.

SEQUENCE LISTING

The instant application contains a Sequence Listing which has been submitted in ASCII format via EFS-Web and is hereby incorporated by reference in its entirety. Said ASCII copy, created on Sep. 22, 2011, is named KlatK US_ST25.txt and is 22.9 kilobytes in size.

BACKGROUND ART

Natural peptides have an important signalling function and coordinate many biochemical processes. Because of this, peptides have become indisputably promising active ingredients, particularly in the cosmetics industry where compounds are continually being sought able to beautify the skin and appendages, i.e. able to improve its general state.

There are many ways in cosmetics of improving the general state of the skin and appendages, in particular enhancing or restoring brightness, moisturising, pigmenting or depigmenting, protecting against harmful external factors such as UV rays or the cold, soothing irritation, redness and acne, reducing oedema (such as bags under the eyes), reducing dark circles, signs of ageing such as wrinkles and fine lines, pigmentation, restoring suppleness and elasticity, treating hair loss, acting on adipose tissue, providing volume and density, improving texture, helping healing, and promoting the growth and quality of the skin appendages, etc.

The action mechanisms of peptides are not always known. Results may be obtained with peptides acting, for example, on the skin's extracellular matrix, particularly by promoting the synthesis of molecules, by preventing their degradation or by acting on receptors. The same peptide sometimes has several simultaneous cosmetic effects.

KXK peptides (lysine-AA-lysine) have been proposed as TGF-beta growth factor activators thereby enabling the synthesis of collagen in the skin extracellular matrix. The peptide proposed in document FR2810323 (Shiseido) is elaidyl-KFK, in which the AA amino acid is phenylalanine.

In document EP1625150 (Pentapharm), the inventors describe elaidyl-KFK as being insufficiently active to stimulate collagen synthesis and propose to alter the lysine side chains, for example the length of the aminated alkyl chains or to introduce specific side chains (functionalised) or to use a central amino acid AA with a hydrocarbon chain possibly substituted by a hydroxyl group. Amongst the examples given, Pal-KVK (where Pal is a palmitoyl lipophilic chain), Pal-KAK or Pal-KSK can be found in the application.

Actually these peptides have been found to be relatively ineffective particularly at the concentrations of a few ppm usually used in cosmetics.

WO 99/12968 and WO 00/42071 disclose peptides, variants, derivatives and analogs and their use in therapeutic methods to inhibit or augment an inflammatory response. Tripeptides KXK, with X one of the twenty naturally occurring amino acids are listed, some of them were tested and being TGF-beta activators and/or chemokine antagonists.

The purpose of the present invention is to propose other peptidic compounds, in particular of the KXK type, for the cosmetic and dermopharmaceutic fields, that are able to improve the general state of the skin and its appendages. In addition, the invention aims to propose peptidic compounds sufficiently effective to be used at low proportions of few ppm.

SUMMARY OF THE INVENTION

To this aim, according to a first object the present invention proposes peptides described by formula I below:

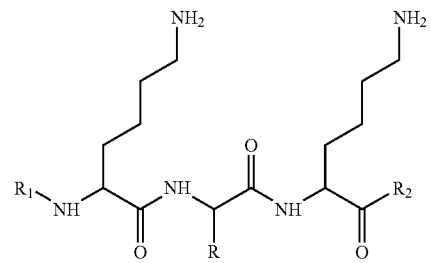

R being a side chain with at least one heteroatom selected from the group consisting of sulfur, nitrogen and oxygen in the form of a carbonyl (C=O);

$R_1$ being either H or a lipophilic chain; and $R_2$ being either OH or a lipophilic chain.

The term "peptides" here includes:
- peptides prepared from coded amino acids;
- analogues obtained from uncoded constituent amino acids; these analogues may be derivatives of coded amino acids or may be synthesized amino acids; and
- salts of these peptides (for example in the form of hydrochlorides or acetates).

One of the specific features of the peptides according to this first object of the invention resides in the fact that they possess a heteroatom, sulfur, nitrogen or oxygen in carbonyl form, in the a position on the side chain R of a central amino acid located between two lysines. These heteroatoms can form hydrogen bonds with other molecules, peptides and/or proteins on application sites and through this can induce biochemical reactions.

In formula I, the side chain according to the invention is a carbon-containing chain which can be linear or branched, saturated or unsaturated.

According to a first aspect, in formula I, the side chain R has a sulfur atom as the heteroatom. In this case, the R group is preferably —$(CH_2)_n$—$SR_3$, where n=0 to 5 and $R_3$=H or an alkyl chain of 1 to 5 carbons which may be linear or branched and saturated or unsaturated According to other specific features which may further increase the possibilities of hydrogen bonds:
the sulfur atom is oxidized (SO/sulfoxide) and preferably dioxidized ($SO_2$/sulfone);
the R group has at least one other heteroatom in order to form an additional chemical group such as, for example, a disulfide bridge or amide group.

The invention therefore covers peptides obtained from coded constituent amino acids, i.e. the following peptides:
$R_1$-KMK-$R_2$ (M being methionine), in which R=—$CH_2$—$CH_2$—S—$CH_3$, and
$R_1$-KCK-$R_2$ (C being cysteine), in which R=—$CH_2$—S—H.

The invention also covers analogous peptides, for example in which:
R=—$CH_2$—$CH_2$—S—H, obtained from homocysteine;
R=—$CH_2$—S—S-tbutyl; R=—S—$SO_2$—ONa or
R=—$CH_2$—S—$CH_2$—NH—CO—$CH_3$, which may be derived from cysteine.

According to a second aspect, in formula I the heteroatom is a nitrogen atom. In this case the R group is preferably —$(CH_2)_n$—$NR_4R_5$, where n=0 to 5 and $R_4$ and $R_5$=H or an alkyl chain of 1 to 5 carbon atoms which may be linear or branched and saturated or unsaturated.

According to other specific features which may further still increase the possibility of hydrogen bonds, the R group possesses at least one other heteroatom in order to form an additional chemical group such as, for example, a urea group.

The invention therefore covers peptides obtained from coded constituent amino acids, i.e. peptides:
$R_1$-KKK-$R_2$ (K being lysine), in which R=—$(CH_2)_4$—$NH_2$; and
$R_1$-KRK-$R_2$ (R being arginine), in which R=—$(CH_2)_3$—NH—C(N=H)$NH_2$.

The invention also covers analogous peptides such as, for example, the peptide in which R=—$(CH_2)_3$—NH—CO—$NH_2$.

According to a third aspect in formula I the heteroatom is an oxygen atom in carbonyl form (C=O). In this case the R group is preferably —$(CH_2)_n$—$COR_6$, with n=0 to 5 and $R_6$ a group such as —$COR_6$ forms a carboxylic acid, an amide or an ester or $R_6$ is such that R forms a urea.

According to other specific features further increasing the possibility of hydrogen bonds, the R group has another heteroatom in order to form an additional chemical group such as, for example, a urea group.

The invention therefore covers peptides obtained from coded constituent amino acids such as aspartic acid, glutamic acid, glutamine and asparagine such as respectively:
peptide $R_1$-KDK-$R_2$ in which R=—$(CH_2)$—COOH,
peptide $R_1$-KEK-$R_2$ in which R=—$(CH_2)_2$—COOH,
peptide $R_1$-KQK-$R_2$ in which R=—$(CH_2)_2$—$CONH_2$,
peptide $R_1$-KNK-$R_2$ in which R=—$(CH_2)$—$CONH_2$.

The invention also covers analogous peptides, for example in which:
R=—$CH_2$—$COOCH_3$,
R=—$(CH_2)_3$—NH—CO—$NH_2$, containing a urea function.

According to a second object, the present invention proposes a compound of formula II below:

in which:
AA is selected from amongst an amino acid, an amino acid derivative and an amino acid analogue;
n=1 to 10, when n≥2, the amino acids may be different and the bonds may be peptide or peptoid;
$R_1$ is H or a lipophilic chain,
$R_2$ is OH or a lipophilic chain,
characterized in that the AA or if n>1 at least one of the amino acids contains at least one oxygenated sulfur atom.

The invention therefore covers:
compounds containing a single amino acid, amino acid derivative or amino acid analogue which has at least one oxygenated sulfur atom; and
peptides or peptoids comprising two to ten amino acid, derivatives or amino acid analogues, at least one of which containing at least one oxygenated sulfur atom, a peptoid being a compound which can contain peptoid bonds analogous to peptide bonds such as ester bonds between certain AA units.

For the purposes of simplification, the term "peptidic compound" is used hereafter for all the possible compounds according to the second aspect of the invention as defined above. The terms oxygenated and oxidized are equivalent.

According to the invention, the peptide or peptidic compound may take the form of the ionic salt. Above ten amino acids, amino acid derivatives or analogues, peptides or peptoids are generally too voluminous for cosmetic applications and also are too expensive to manufacture. For these reasons the peptide compound according to the invention may advantageously be limited to six amino acid AA units.

According to the invention, the term amino acid derivative refers to compound obtained by chemical modification of existing amino acids, particularly coded amino acids. Examples of amino acid derivatives particularly useful for being oxygenated include derivatives of methionine, alkylated cysteines derived from cysteine, alkylated derivatives of homocysteine, or derivatives of threonine and serine in which the alcohol function is replaced by a —S-alkyl function, preferably —S—$CH_3$.

According to the invention, the term amino acid analogues refers to compounds having chemical analogies with coded amino acids, such as hydroxy acids which have an alcohol group in place of the amine group or β-amino acids which have a β side chain with regard to the carboxylic acid group, or more broadly, small molecules simultaneously comprising an amine group and a carboxylic acid group. Examples include in particular "hydroxymethionine" which has an OH alcohol group in place of the $NH_2$ amine group in a methionine or 5-amino valeric acid (Ava) of formula $NH_2$—$(CH_2)_4$—COOH. In vitro tests described below show that such peptide compounds whether or not containing several amino acid, amino acid derivative or amino acid analogue AA units, at least one of these AA units comprising an oxygenated sulfur atom, have cosmetic activity, particularly by stimulating collagen I synthesis in the skin extracellular matrix. An oxygenated sulfurized derivative of molecule such as Ava can be used according to the invention, where the $SO_2$ function is located either on the hydrocarbon chain between the amine and carboxylic functions or on a additional hydrocarbon side chain (examples are given below).

Furthermore, the present invention also concerns a method for enhancing the activity of a peptide compound, characterized by the step consisting of introducing at least one oxygenated sulfur atom in one of the amino acid of said peptidic compound. The step of introducing an oxygenated sulfur atom may consist in oxygenating at least one of the sulfur atoms present in one of the amino acid of said peptidic compound, in introducing an amino acid containing at least one oxygenated sulfur atom, and/or in replacing an amino acid by an amino acid containing at least one oxygenated sulfur atom.

Thus, according to the invention, at least one sulfur atom may be beneficially included in a compound containing at least one amino acid, amino acid derivative or amino acid analogue.

Starting from known peptide compounds the inventors have demonstrated amplified cosmetic activity by introducing oxygenated sulfur. This introduction may be made by oxygenating one or more sulfur atoms contained in one of the AA units. This applies for example to the case of known peptides containing a methionine which is beneficially converted according to the invention into oxygenated methionine. One or more additional amino acids, amino acid derivatives or amino acid analogues including one or more oxygenated sulfur atoms can also be introduced into a known peptide.

Oxygenating the existing sulfur atoms in a peptide compound also beneficially reduces the "sulfurous" smell of the compound.

In addition, thanks to the invention, simpler peptide compounds (fewer AA and therefore less expensive) may be designed, the cosmetic activity of these compounds being due to the presence of the oxygenated sulfur.

The bonds between the AA units are, depending on the molecule, either peptide, peptoid or mixed.

Depending on the molecule, in the oxygenated sulfur containing AA, the sulfur atom or atoms are preferably di-oxygenated, providing greater stability to the final compound.

Preferably also, the oxygenated sulfur atom according to the invention is located on a hydrocarbon side chain of the AA unit, also preferably a side chain in the $\alpha$ or $\beta$ position with respect to the COOH group.

According to a particularly useful feature of the invention therefore, the at least one amino acid which has a sulfur atom oxygenated is selected from methionine, methionine derivatives, cysteine derivatives, homocysteine derivatives, threonine derivatives, serine derivatives and their hydroxy acid analogues.

More preferably the AA is an oxygenated methionine and preferably a di-oxygenated methionine. Methionine has the advantage of being a natural coded amino acid which is inexpensive and easy to oxidize into the sulfone.

Results on beautifying and on the general state of the skin and of its appendages have therefore been seen with the peptides or peptidic compounds according to the invention, in particular:

texture: the moisturising capacity of the skin is improved, the skin is less rough and softer and skin water loss is reduced; the skin is better protected against external aggressions;

mechanical properties: the skin is denser, replumped, firmer, more toned and therefore more elastic; the peptide has a volume-producing, replumping effect.

In addition, the inventors have also found the following effects:

slimming, particularly by reducing expansion and/or preventing the development of adipose tissue,
antioxidant;
effects on the visible appearance of the skin: skin is brighter, the complexion is more uniform, pigmentation spots and redness are less visible and dark circles are reduced;
effects on the general appearance of the hair: hair is thicker, smoother, less dull, hair loss is reduced and regrowth is improved; moisturisation of the scalp is improved and dandruff formation is reduced;
on the general appearance of the eyelashes: thicker, reduced loss and improved regrowth.

As a result, applications can be proposed particularly in the ranges relating to moisturising, make-up removal, anti-ageing, anti-oxidising, protective, slimming, repairing (hands, feet, lips), contours (face, eyes, neck, lips), treatment-make-up for both the skin and its appendages, particularly ranges for the eyelashes, lip products, sun care products, remodelling, plumping, volume-enhancing (for example in the hands, bust, breasts) and hair care products, etc.

More specifically, using in vitro tests, the inventors have demonstrated better results on collagen I synthesis in the dermis obtained by the peptide or peptidic compound according to the invention at concentrations of a few ppm.

Other molecules of the dermis and epidermis are also stimulated, including molecules involved in the dermal-epidermal junction:

in the dermis, particularly collagen III, collagen IV, fibronectin and hyaluronic acid; and
in the epidermis, particularly laminins, fibronectin and hyaluronic acid.

Collagen III forms similar fibrils to collagen I which confer very high resistance to traction and inextensibility to the connective tissue.

Collagen IV forms a two-dimensional network and is one of the main components of the dermo-epidermal junction.

Laminins are also present in the basal layer and take part in anchoring cell surfaces to the basal lamina.

Increases in collagen IV and laminins according to the invention therefore contribute beneficially to restoring the dermo-epidermal junction.

Fibronectin forms "adhesive" elastic fibres, the particular role of which is to attach cells to the extracellular matrix. It is involved in strengthening the mechanical properties of the skin, particularly suppleness and elasticity.

Hyaluronic acid is one of the main constituents of the dermis and epidermis; it has a very great capacity to bind and retain water.

The inventors have also demonstrated stimulation of CD44 protein in the epidermis. This protein acts, in particular, to anchor hyaluronic acid in the extracellular matrix. Transit water bound by hyaluronic acid is therefore better retained in the skin.

The inventors have also demonstrated stimulation of the synthesis of aquaporins which also play a major role in the control of moisturisation.

Furthermore, according to the invention, using a "DNA Array" test an increase has been found in the production of genes associated with lipid barrier effect metabolism, also contributing to protect the skin and combat skin water loss.

The peptide or peptidic compounds of the invention therefore beneficially have very great potential in the field of cosmetics and dermopharmacy.

Prevention and/or treating of the signs of skin aging, protection and/or improving skin condition, and the prevention and/or treatment of skin imperfections are functional features which can be analyzed, measured and quantified using many techniques known by the specialist in cosmetic treatments.

Decrease of lines and wrinkles and of skin roughness can be quantified either directly on the person using a relief obtaining system without contact using fringe projection (FOITS=Fast Optical In vivo Topometry System, Dermatop™ or Primos™ system), or by silicon fingerprints which are then analyzed by the technique called "drop shadows" or by a FOITS system using a VISIA® device.

Improvement of the skin microdepressionary network (NMD) and of skin isotropy are quantified by silicon fingerprints which are then analyzed by the technique called "drop shadows" or by a FOITS system.

Changes in volume and shape of the face can be quantified using a relief obtaining system without contact using a fringe projection FOITS system.

Skin dryness or hydration is directly measurable by electrical techniques: Corneometer™ Moisturemeter™, Dermalab™ devices; or by optical techniques: near infrared spectroscopy (NIR); or indirectly using the D-Squames® technique or image analysis on photo technique.

Alteration of the skin barrier can be quantified by measuring transepidermal water loss (TEWL) using a Tewameter™, a Vapometer™, a Dermalab™ or an Aquaflux™ device.

The pH, also important to quantify the alteration of the skin barrier, can be measured using a pH meter dedicated to the skin.

Decrease of seborrhea is studied directly using Sebutape™ or an optical device as a Sebumeter™ or Dermalab™ device or indirectly by analysis of porphyrins under UV light seen by a VISIA® device, or also indirectly by specific analysis of the brightness either with devices such as a Skinglossmeter™ or using photos (enabled by the technique of photographing in polarized crossed and parallel light).

Loss of firmness and/or elasticity and/or tone and fatigue of the skin can be quantified using a Cutometer™, a Reviscometer™, an Aeroflexmeter™, a Dynaskin™, a Ballistometer™, a Twistometer™ and/or a Dermalab™ device.

Dull complexion, loss of uniformity of skin tone, pigmentation changes (hypo and hyper pigmentation), local reddening, loss of clarity and brightness of the complexion, pigmentation spots, rosacea, dark circles are directly measurable using a Mexameter™, a Chromameter™, a Colormeter™, a VISIA®, a SIAscope™, a Goniolux™ or a confocal laser microscope device or by specific color analysis on photo (enabled by the technique of photographing in polarized crossed and parallel light).

Sunspots visible under UV can be quantified by a VISIA® device.

The number and size of facial pores can be quantified by silicon fingerprints which are then analyzed by the technique called "drop shadows" or by a FOITS system, or by a Canfield VISIA® device or by specific analysis on photo (enabled by using a video microscope or a macroscopic photographing system).

Thinning of the skin, dermis or hypodermis (the study of slimming agents) is measurable by an ultrasound echographic device.

Thickness of the stratum corneum can be quantified by terahertz Spectroscopy.

Density of skin fibers can be quantified by ultrasound and then by image analysis.

Cellulite is quantified either directly by a relief obtaining system without contact using fringe projection (FOITS) or indirectly by measuring the length of the dermohypodermal junction by an ultrasound echographic device.

Stretch marks are either directly quantified using a relief obtaining system without contact using fringe projection (FOITS) or by silicon fingerprints which are then analyzed by the technique called "drop shadows" or by the FOITS system, or using a VISIA® device.

Water retention (associated with cellulite) can be quantified with a Moisturemeter-D™

Decrease or increase in skin microcirculation, as well as soothing or irritation can be analyzed using a laser Doppler, using "capilaroscopy" (using a video microscope) or using an infrared camera.

Hair growth speed (beard, legs, arm pits) can be quantified by an adaptation of the "videotrichogrammy".

Skin thermoregulation can be quantified by analysis of changes in skin temperature, measured directly by temperature sensors or indirectly by an infrared camera.

Skin wettability (hydrophobic or hydrophilic features) is measurable by the technique of the diameter or the contact angle of a drop deposited on the skin.

Stratum corneum renewal (or scaling) can be quantified by measuring the time of skin discoloration after a marking (with dansyl chloride or dihydroxyacetone).

Skin sensitivity can be quantified by the technique of the Stinging Test or by a neurometer device.

Changes in collagen and/or in connective tissue fibers may be quantified by UV spectroscopy, by SIAscopie, by multiphoton spectroscopy or by confocal laser microscopy.

Stratum corneum composition and the monitoring of certain molecules (water, NMF) can be evaluated by Raman spectroscopy.

Visualization at a cellular level in the skin can be done with laser confocal microscopy with multiphoton microscopy, with NMR, or to a lesser extent with optical coherence tomography (OCT).

Changes in water and lipid contents can be evaluated in vivo by Fourier Transformation in vivo Infra-red spectroscopy (FTIR HATR=Fourier Transformation Infra Red Horizontally Attenuated Total Reflection).

Skin softness is directly measurable by techniques of friction study as with a frictiometer device or indirectly by silicon fingerprints which are then analyzed by the technique called "drop shadows" or by a FOITS system.

All changes visible to the eye (reliefs, color) can be quantified in direct or on photography, by a trained judge person or not, with or without quotation system.

The peptide or peptidic compound of the invention may be optically pure or may be formed from the L or D isomers or a mixture of these isomers. In the case of a peptide or peptidic compound formed from coded amino acids, the L isomers which are those present in the natural state may be preferred as they are less expensive.

In addition, the peptide according to the first object of the invention or the peptide compound according to the second object of the invention may be a fragment of a larger peptide compound.

As known per se, in general formula I of the peptide according to the first object of the invention and in general formula II of the peptide compound of the second object, the lipophilic chain or chains $R_1$ and $R_2$ have the function of improving the bioavailability of the compound and its skin penetrating capacity.

As can be seen in particular on formula I, in a conventional and known per se manner, $R_1$ is a group located at the N-terminal end of the peptidic compound, substituting one of the hydrogen atom of the amine terminal function of the "first" amino acid (conventionally on the left side of the formula), whereas the $R_2$ is a group located at the C-terminal end of the peptidic compound, linked to the carbonyl function of the "last" amino acid (conventionally on the right side of the formula).

A lipophilic chain $R_1$ is usually an acyl or sulfonyl group such as a biotinoyl group or a group containing an alkyl, aryl, aralkyl, sugar or alkoxy chain of 1 to 24 carbon atom which may in particular be linear, branched or cyclical, saturated or unsaturated, hydroxylated or unhydroxylated, sulphur-containing or non-sulphur-containing.

$R_1$ may, for example, be selected from amongst acetyl ($CO-CH_3$), palmitoyl (pal=$CO-(CH_2)_{14}CH_3$), elaidoyl, myristoyl ($CO-(CH_2)_{12}-CH_3$), biotinoyl, octanoyl, stearoyl, oleoyl and lipoyl groups.

A lipophilic chain $R_2$ is usually an $-O-R_7$ group or a $-NR_8R_9$, $R_7$, $R_8$ and $R_9$ group being independent from one another, a hydrogen or an alkyl, aryl, aralkyl, acyl, sulfonyl, sugar or alkoxy chain of 1 to 24 carbon which is linear, branched or cyclical, substituted or unsubstituted, saturated or unsaturated, hydroxylated or unhydroxylated and sulphur-containing or non-sulphur-containing.

Preferably, $R_1$ is a lipophilic chain and $R_2$ is a hydroxyl. Even more preferably $R_1$ is a palmitoyl (hereafter called "Pal"), acetyl or elaidoyl group.

Therefore, a preferred peptide according to the invention is the Pal-KMO2K-OH in which the methionine comprises a sulfur atom which is dioxygenated, this peptide presenting results and properties particularly interesting in particular for cosmetic and dermopharmaceutical applications.

Examples of compounds according to the second object of the invention responding to formula II are given thereafter.

1) Examples of Compounds Having One AA Unit which is Therefore Sulfurized and Oxygenated:

$R_1$-MO2-$R_2$: AA is MO2, a methionine which has a dioxigenated sulfur atom.

With $R_1$=a Pal chain and $R_2$=$NH_2$ the compound presents the following structure:

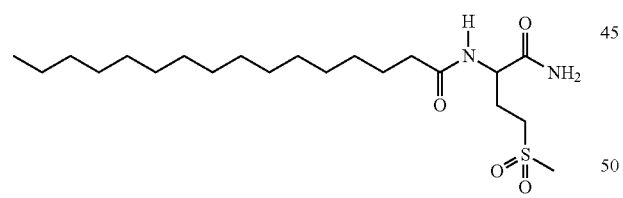

$R_1$—HAO2-$R_2$: AA is a dioxigenated sulfurized hydroxy-acid (HAO2), a methionine analogue in which the amine function is replaced by an alcohol function.

With $R_1$=H and $R_2$=OH the compound presents the following structure:

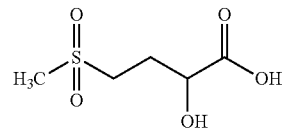

$R_1$-MetCO—$R_2$: AA is methylated cysteine derivative (MetC) having a monoxigenated sulfur atom.

With $R_1$=a Pal chain and $R_2$=OH the compound presents the following structure:

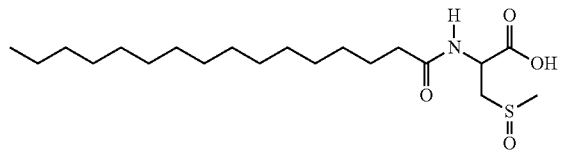 [SMILES: CCCCCCCCCCCCCCCC(=O)NC(CS(C)=O)C(=O)O]

$R_1$-EtHCO$_2$—$R_2$: AA is an ethylated derivative of the homocysteine (EtHC) which sulfur atom is dioxygenated according to the invention.

With $R_1$=a Pal chain and $R_2$=$NH_2$ the compound presents the following structure:

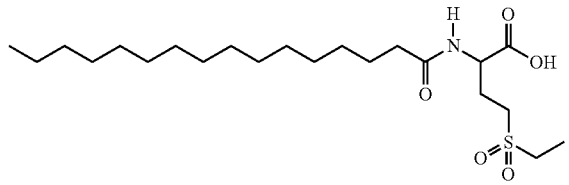 [SMILES: CCCCCCCCCCCCCCCC(=O)NC(CCS(=O)(=O)CC)C(=O)O]

$R_1$—$CH_3$SOT-$R_2$: AA is a threonine derivative, the alcohol function being substituted by a $SO-CH_3$ function.

With $R_1$=a Pal chain and $R_2$=OH the compound presents the following structure:

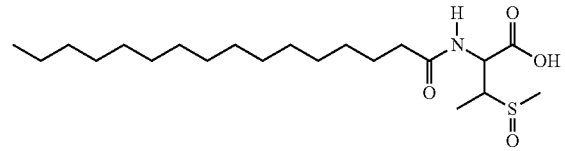 [SMILES: CCCCCCCCCCCCCCCC(=O)NC(C(=O)O)C(C)S(C)=O]

$R_1$-AvaSO2-$R_2$: Ava02 is the 5-amino valeric acid ($NH_2-(CH_2)_4-COOH$) having a S02 substituting a carbon atom of the hydrocarbon chain, preferably on the 3 or $4^{th}$ position.

With $R_1$=a Pal chain and $R_2$=OH the compound presents the following structure:

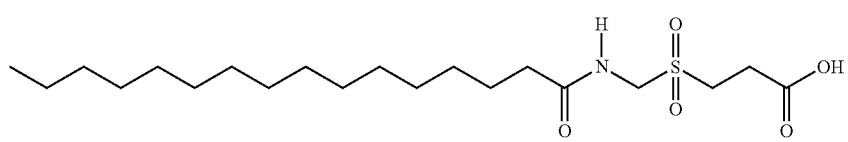 [SMILES: CCCCCCCCCCCCCCCC(=O)NCS(=O)(=O)CCC(=O)O]

R$_1$-AvaSO2CH3-R$_2$: Ava02 is the 5-amino valeric acid (NH$_2$—(CH$_2$)$_4$—COOH) having a S02alkyl lateral group (here a CH3) on the hydrocarbon chain, preferably on the 3 or 4$^{th}$ position.

With R$_1$=a Pal chain and R$_2$=OH the compound presents the following structure:

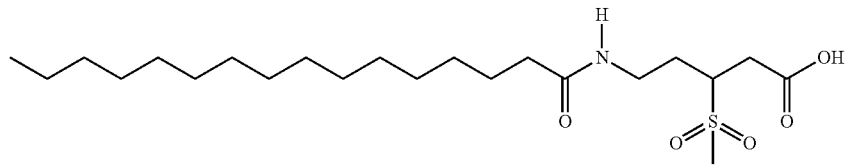 [SMILES: CCCCCCCCCCCCCCCC(=O)NCCC(CC(=O)O)S(C)(=O)=O]

2) Examples of Compounds Having Two AA Units (which can Possess Either Only One Oxygenated Sulfurized AA or Two Oxygenated Sulfurized AA).

R$_1$-MO2-K-R$_2$

With R$_1$=a Pal chain and R$_2$=OH the compound presents the following structure:

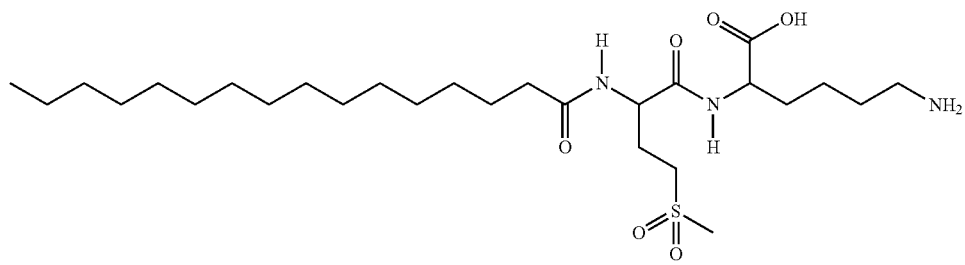 [SMILES: CCCCCCCCCCCCCCCC(=O)NC(CCS(C)(=O)=O)C(=O)NC(CCCCN)C(=O)O]

R$_1$-K-MO2-R$_2$

With R$_1$=a Pal chain and R$_2$=NH$_2$ the compound presents the following structure:

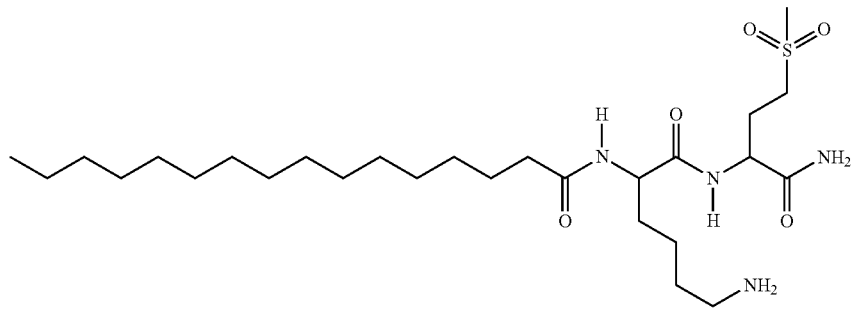 [SMILES: CCCCCCCCCCCCCCCC(=O)NC(CCCCN)C(=O)NC(CCS(C)(=O)=O)C(N)=O]

R$_1$-MO2-Ava-R$_2$

With R$_1$=a Pal chain and R$_2$=NH$_2$ the compound presents the following structure:

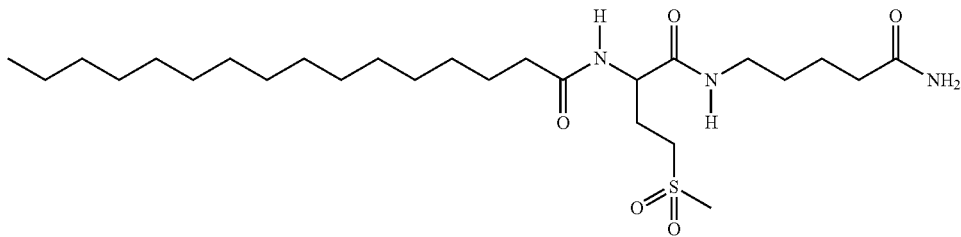 [SMILES: CCCCCCCCCCCCCCCC(=O)NC(CCS(C)(=O)=O)C(=O)NCCCCC(N)=O]

$R_1$-Ava-MO2-$R_2$
With $R_1$=a Pal chain and $R_2$=$NH_2$ the compound presents the following structure:

Oxygenation of the known peptide $R_1$-K-T-F-K-$R_2$ (SEQ ID NO 5)

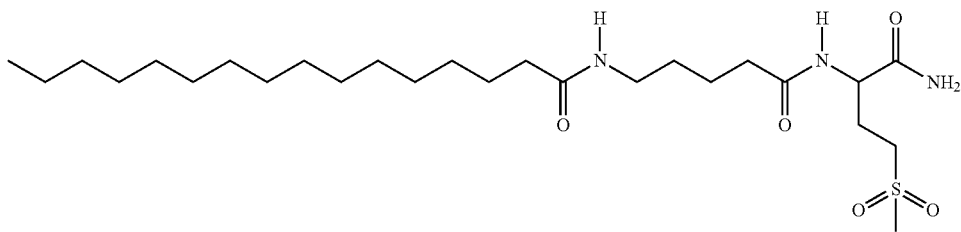 [SMILES: CCCCCCCCCCCCCCCC(=O)NCCCCC(=O)NC(CCS(C)(=O)=O)C(N)=O]

3) Examples of Compounds Having 3 AA:

$R_1$-K-MO2-K-$R_2$

Oxygenation of the known peptide $R_1$-K-Ava-K-$R_2$ (replacement of one of the AA amino acid unit by a MO2 a methionine with a dioxygenated sulfur atom):

$R_1$-MO2-Ava-K-$R_2$ $R_1$-K-Ava-MO2-$R_2$

4) Examples of Compounds Having 4 AA:

$R_1$-K-MO2-MO2-K-$R_2$.          (SEQ ID NO 1).

Oxygenation of the known peptide $R_1$-K-Ava-K-$R_2$ (addition of a methionine with a dioxygenated sulfur atom in the peptide):

$R_1$-K-MO2-Ava-K-$R_2$.          (SEQ ID NO 2).

$R_1$-K-Ava-MO2-K-$R_2$.          (SEQ ID NO 3).

$R_1$-MO2-K-Ava-K-$R_2$.          (SEQ ID NO 4).

replacement of one of the AA amino acid unit by a MO2 a methionine with a dioxygenated sulfur atom:

$R_1$-K-MO2-F-K-$R_2$.            (SEQ ID NO 6).

$R_1$-K-T-MO2-K-$R_2$.            (SEQ ID NO 7).

$R_1$-K-T-F-MO2-$R_2$.            (SEQ ID NO 8).

$R_1$-MO2-T-F-K-$R_2$.            (SEQ ID NO 9).

Other possible oxygenated peptides with AA selected from K, T, F and MO2 as the dioxygenated AA.

$R_1$-K-MO2-T-K-$R_2$.            (SEQ ID NO 10).

$R_1$-K-F-MO2-K-$R_2$.            (SEQ ID NO 11).

$R_1$-K-T-MO2-F-$R_2$.            (SEQ ID NO 12).

Oxygenation of the known tetrapeptide $R_1$-G-Q-P-R-$R_2$ (SEQ ID NO 13)

replacement of one of the AA amino acid unit by a MO2 a methionine with a mono-oxygenated sulfur atom:

$R_1$-G-MO-P-R-$R_2$.             (SEQ ID NO 14).

insertion of a MO2 a methionine with a dioxygenated sulfur atom and the R amino acid is removed:

R$_1$-G-MO2-Q-P-R$_2$.    (SEQ ID NO 15).

Oxygenation of the known tripeptide R$_1$-G-H-K-R$_2$ (addition of a MO2 a methionine with a dioxygenated sulfur atom):

R$_1$-MO2-G-H-K-R$_2$.    (SEQ ID NO 16).

5) Examples of Compounds Having 5 AA:
Oxygenation of the known peptide R$_1$-G-Q-P-R-R$_2$ (SEQ ID NO 13) (addition of a methionine with a monoxygenated sulfur atom in the peptide):

R$_1$-MO-G-Q-P-R-R$_2$.    (SEQ ID NO 17).

Oxygenation of the known peptide R$_1$-K-T-T-K-S-R$_2$ (SEQ ID NO 18) (replacement of a threonine T by CH$_3$SOT, as recited above):

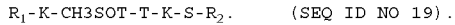
R$_1$-K-CH3SOT-T-K-S-R$_2$.    (SEQ ID NO 19).

Oxygenation of the known peptide R$_1$-K-T-T-K-S-R$_2$ (SEQ ID NO 18) replacement of a threonine by a methionine having a dioxygenated sulfur atom:

R$_1$-K-MO2-T-K-S-R$_2$.    (SEQ ID NO 20).

replacement of a lysine by a methionine having a dioxygenated sulfur atom:

R$_1$-MO2-T-T-K-S-R$_2$.    (SEQ ID NO 21).

oxygenation of the serine by replacing the serine S by methylated form in which the sulfur atom is dioxygenated:

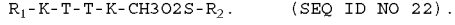
R$_1$-K-T-T-K-CH3O2S-R$_2$.    (SEQ ID NO 22).

6) Examples of Compounds Having 6 AA:
Oxygenation of the known peptide R$_1$-K-T-T-K-S-R$_2$ (SEQ ID NO 18) (addition of a methionine having a dioxygenated sulfur atom in the peptide):

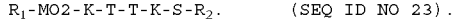
R$_1$-MO2-K-T-T-K-S-R$_2$.    (SEQ ID NO 23).

Obviously, the present invention is not limited to those examples but covers a lot of variants, in particular regarding the type of AA amino acid unit, regarding the degree of oxygenation (SO or SO$_2$), the number of oxygenated AA unit, their row in the peptide compound, etc.

The present invention aims also the cosmetic and dermopharmaceutical compositions comprising the compounds according to first and second object of the invention and the applications/uses recited above.

As known per se, the peptide according to the first object of the present invention and the peptidic compound according to the second object of the invention can be manufactured either by conventional chemical synthesis (in heterogeneous or homogeneous phase) or by enzymatic synthesis from amino acids or constituent analogues, followed where applicable by bonding a lipophilic chain onto the terminal amino acid in question. They can also be obtained by hydrolysis of natural proteins or by a biotechnology process.

According to the invention, a cosmetic composition is proposed incorporating the peptide according to the first object of the invention or the peptidic compound according to the second object of the invention, as the active ingredient, combined with an appropriate excipient, i.e. a physiologically or dermatologically acceptable medium.

According to this invention the term "dermatological or physiological medium" means, but is not restricted to, an aqueous or aqueous-alcoholic solution, a water in oil emulsion, an oil in water emulsion, a micro-emulsion, an aqueous gel, an anhydrous gel, a serum, a dispersion of vesicles. "Dermatologically acceptable" or "physiologically acceptable" means that the compositions or compounds derived are suitable for use in contact with mammal, and more particularly human, mucosal membranes, nails, scalp, head hair, body hair and skin without risk of toxicity, incompatibility, instability, allergic response or others.

The peptide of the first object or the peptidic compound of the second object is present in the composition in proportions of between 0.000001% and 15% of the total weight of the composition, more preferably between 0.0001% and 5%, depending on the destination of the composition and the more or less potent effect sought.

All of the percentages and ratios used in this application are by weight of the total composition and all measurements are performed at 25° C. unless stated otherwise.

Typically, in a cosmetic composition according to the invention formed simply from the peptide or the peptidic compound of the invention and an excipient used to dissolve it, forming for example an "active ingredient" for the future preparation of a cosmetic composition, the amount of peptide or of peptidic compound will be between 0.00005% and 0.005%.

The choice of excipient for the composition is made depending on the constraints relating to the peptide or peptidic compound (stability, solubilisation, etc.) and, where applicable, the galenic form subsequently envisaged for the composition.

The peptide or peptidic compound may, for example, take the form of a solution, dispersion, emulsion, paste or powder, individually or premixed or carried individually, or as a premixture by carriers such as macrocapsules, microcapsules, nanocapsules, macrospheres, microspheres or nanospheres, liposomes, oleosomes or chylomicrons, macroparticles, microparticles or nanoparticles, macrosponges, microsponges or nanosponges, microemulsions or nanoemulsions or absorbed onto powderous organic polymers, talcs, bentonites and other mineral or organic supports.

According to other beneficial features, the cosmetic or dermopharmaceutical composition according to the invention may incorporate one or more additional active ingredients, beneficially enabling a cosmetic product to be obtained with a wider still range of properties. The additional active ingredients may be selected from brightening, anti-redness agents, sunscreens and UV organic or inorganic filters, hydration, moisturizing, humectants, exfoliants, anti-wrinkle, anti-ageing, slimming, anti acne, anti inflammatory, anti-oxidant, radical scavenger, self tanning, depilation or shave, hair growth moderator, tightening agents, peptides and vitamins. The active ingredients can be obtained from plant material.

Possible active ingredients are given in the detailed description given below.

More specifically, the peptides or peptidic compounds of the present invention may be combined with at least one compound selected from vitamin $B_3$ compounds like niacinamide or tocopherol, retinol, hexamidine, α-lipoic acid, resveratrol and DHEA, which are classical active ingredients in the cosmetic fields.

In addition, the composition may also include betaine, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Essenskin™ (Sederma), Moist 24™ (Sederma), Argireline™, the commercial name of acetyl hexapeptide-3 (Lipotec), spilanthol or an extract of *Acmella oleracea* known by the name Gatuline Expression™ (EP 1722864), extract of *Boswellia serrata* known by the name Boswellin™, Deepaline PVB™ (Seppic), Syn-AKE™ (Pentapharm), Ameliox™, Bioxilift™ (Silab) and mixtures thereof.

Among other plant extracts which can be combined with the compounds of the invention, there may more particularly be mentioned extracts of Ivy, in particular English Ivy (*Hedera Helix*), of Chinese thorowax (*Bupleurum chinensis*), of *Bupleurum Falcatum*, of arnica (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum Perforatum*), of butcher's-broom (*Ruscus aculeatus* L), of European meadowsweet (*Filipendula ulmaria* L), of bigflowered Jarva tea (*Orthosiphon Staminceus Benth*), of algae (*Fucus Vesiculosus*), of birch (*Betula alba*), of green tea, of cola nuts (*Cola Nipida*), of horse-chestnut, of bamboo, of spadeleaf (*Centella asiatica*), of heather, of fucus, of willow, of mouse-ear, of escine, of cangzhu, of *chrysanthellum indicum*, of the plants of the *Armeniacea* genus, *Atractylodis Platicodon, Sinnomenum, Pharbitidis, Flemingia*, of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, of *Guioa*, of *Davallia*, of *Terminalia*, of *Barringtonia*, of *Trema*, of *antirobia, cecropia, argania, dioscoreae* such as *Dioscorea opposita* or Mexican, extracts of *Ammi visnaga*, of *Centella asiatica* and *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, *Piper methysticum* extract (Kava Kava from SEDERMA (FR 2 771 002 and WO 99/25369), *Bacopa monieri* extract (Bacocalmine™ from SEDERMA, WO 99/40897) and sea whip extract, extracts of *Glycyrrhiza glabra*, of mulberry, of *melaleuca* (tea tree), of *Larrea divaricata*, of *Rabdosia rubescens*, of *euglena gracilis*, of *Fibraurea recisa Hirudinea*, of *Chaparral Sorghum*, of sun flower extract, of *Enantia chlorantha*, of Mitracarpe of *Spermacocea* genus, of *Buchu barosma*, of *Lawsonia inermis* L., of *Adiantium Capillus-Veneris* L., of *Chelidonium majus*, of *Luffa cylindrical*, of Japanese Mandarin (*Citrus reticulata* Blanco var. *unshiu*), of *Camelia sinensis*, of *Imperata cylindrical*, of *Glaucium Flavum*, of *Cupressus Sempervirens*, of *Polygonatum multiflorum*, of *loveyly hemsleya*, of *Sambucus Nigra*, of *Phaseolus lunatus*, of *Centaurium*, of *Macrocystis Pyrifera*, of *Turnera Diffusa*, of *Anemarrhena asphodeloides*, of *Portulaca pilosa*, of *Humulus lupulus*, of *Coffea Arabica* and of *Ilex Paraguariensis*.

As a particular example, but not to be limited to, the peptide or peptidic compound of the invention can be combined with an extract of *Portulaca pilosa*. This plant also called "Kiss me quick" or "Amor Crescido" is part of the purslane family. It is a small edible oily plant rich in omega 3, vitamins A, $B_1$, $B_2$ and C and mucilage. It is used in cosmetics for its particular anti-inflammatory, soothing, softening and lightening properties and to treat hair (to give it volume and stimulate regrowth). When mixed with the peptide or peptide compound according to the invention, through a synergistic effect it results in an active ingredient with increased activity, as shown by the in vitro results below.

Extraction from the plant may be performed using conventional techniques such as phenolic extraction, from any part of the plant such as the flower, seed, fruit, root, tubercle, leaf, pericarp and preferably rhizome. The extraction solvents may be selected from amongst water, propylene glycol, butylene glycol, glycerine, PEG-6 caprylic/capric glycerides, polyethylene glycol, methyl and/or ethyl esters, diglycols, cyclical polyols, ethoxylated or propoxylated diglycols, alcohols (methanol, ethanol, propanol, and butanol) or any mixture of these solvents. Plant extracts according to the present invention may also be obtained by other processes such as maceration, simple decoction, lixiviation, reflux extraction, supercritical extraction with $CO_2$, ultrasound or microwave extraction or counter-current techniques. This list is not restrictive.

The excipient for the plant extract is selected in order to be compatible with the peptide or peptidic compound and if necessary compatible with an excipient for the peptide or peptidic compound with which the extract will subsequently be mixed and also to be compatible with the physical or galenic form of the final mixture which is to be obtained.

DETAILED DESCRIPTION

The present invention will be better understood from the following description.

The term "cosmetic composition" or simply "composition" according to the present invention, concerns a formulation which may be used for cosmetic or hygiene purposes or as a base for one or more pharmaceutical ingredients. These also include cosmetics, personal care products and pharmaceutical preparations. It is also possible that these formulations may be used for two or more purposes at the same time. A medical anti-dandruff shampoo, for example, has pharmacological properties and is used as a personal care product to obtain healthy hair.

Some compositions from the present invention may also provide additional benefits including stability, lack of significant irritation of the skin (unacceptable to the consumer), anti-inflammatory activity and good aesthetics.

I. ADDITIVES

The compositions of the invention may include various additional other ingredients, conventional or not. Of course, a decision to include an additional ingredient and the choice of a specific active ingredient and of additional ingredients depends on the specific application and product formulation.

The line of demarcation between an "active" ingredient and an "additional" ingredient is therefore artificial and depends on the specific application and product type. A substance that is an "active" ingredient in one application or product may be a "functional" ingredient in another, and vice versa.

The compositions of the invention may include one or more additional ingredients, various, conventional or not, which will provide some benefit to the object of the composition. Such additional ingredients may include one or more substances such as, without limitations, cleaning agents, hair conditioning agents, skin conditioning agents, hair styling agents, antidandruff agents, hair growth promoters, perfumes, sunscreen and/or sunblock compounds, pigments, moisturizers, film formers, hair colors, make-up agents, detergents, pharmaceuticals, thickening agents, emulsifiers, humectants, emollients, antiseptic agents, deodorant actives, surfactants and propellants.

In a preferred embodiment, where the composition is to be in contact with human keratinous tissue, the additional ingredients should be suitable for application to keratinous tissue, that is, when incorporated into the composition they are suitable for use in contact with human keratinous tissue (hair, nails, skin, lips) without undue toxicity, incompatibility, instability, allergic response, and the like within the scope of sound medical judgment.

The CTFA Cosmetic Ingredient Handbook, Tenth Edition (published by the Cosmetic, Toiletry, and Fragrance Association, Inc., Washington D.C.) (2004) describes a non limited wide variety of cosmetic and pharmaceutical ingredients usually used in the skin care industry that can be used as additional ingredients in the compositions of the present invention. Examples of these ingredient classes include, but are not limited to: healing agents, skin anti-aging agents, skin moisturizing agents, anti-wrinkle agents, anti-atrophy agents, skin smoothing agents, antibacterial agents, antifungal agents, pesticides anti parasitic agents, antimicrobial agents, anti-inflammatory agents, anti-pruriginous agents, external anaesthetic agents, antiviral agents, keratolytic agents, free radicals scavengers, antiseborrheic agents, antidandruff agents, the agents modulating the differentiation, proliferation or pigmentation of the skin and agents accelerating penetration, desquamating agents, depigmenting or propigmenting agents, antiglycation agents, tightening agents, agents stimulating the synthesis of dermal or epidermal macromolecules and/or preventing their degradation; agents stimulating the proliferation of fibroblasts and/or keratinocytes or stimulating the differentiation of keratinocytes; muscle relaxants; antipollution and/or anti-free radical agents; slimming agents, anticellulite agents, agents acting on the microcirculation; agents acting on the energy metabolism of the cells; cleaning agents, hair conditioning agents, hair styling agents, hair growth promoters, sunscreen and/or sunblock compounds, make-up agents, detergents, pharmaceutical drugs, emulsifiers, emollients, antiseptic agents, deodorant actives, dermatologically acceptable carriers, surfactants, abrasives, absorbents, aesthetic components such as fragrances, colorings/colorants, essential oils, skin sensates, cosmetic astringents, anti-acne agents, anti-caking agents, anti foaming agents, antioxidants, binders, biological additives, enzymes, enzymatic inhibitors, enzyme-inducing agents, coenzymes, plant extracts, plant derivatives, plant tissue extracts, plant seed extracts, plant oils, botanicals, botanical extracts, ceramides, peptides, buffering agents, bulking agents, chelating agents, chemical additives, colorants, cosmetic biocides, denaturants, drug astringents, external analgesics, film formers or materials, e.g., polymers, for aiding the film-forming properties and substantivity of the composition, quaternary derivatives, agents increasing the substantivity, opacifying agents, pH adjusters, propellants, reducing agents, sequestrants, skin bleaching and lightening agents, skin tanning agents, skin-conditioning agents (e.g., humectants, including miscellaneous and occlusive), skin soothing and/or healing agents and derivatives, skin treating agents, thickeners, and vitamins and derivatives thereof, peeling agents, moisturizing agents, curative agents, lignans, preservatives, UV absorbers, a cytotoxic, an antineoplastic agent, a fat-soluble active, suspending agents, viscosity modifiers, dyes, nonvolatile solvents, diluents, pearlescent aids, foam boosters, a vaccine, and their mixture.

Said additional ingredient is selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, peptides and their derivatives, di-, tri-, tetra-, penta-, and hexapeptides and their derivatives, lys-thr-thr-lys-ser (SEQ ID NO 24), palmitoyl-lys-thr-thr-lys-ser (SEQ ID NO 24), carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins their salts and derivatives, provitamins and their salts and derivatives, ethyl panthenol, vitamin B, vitamin B derivatives, vitamin B1, vitamin B2, vitamin B6, vitamin B12, vitamin K, vitamin K derivatives, pantothenic acid and its derivatives, pantothenyl ethyl ether, panthenol and its derivatives, dexpanthenol, biotin, amino acids and their salts and derivatives, water soluble amino acids, asparagine, alanine, indole, glutamic acid, water insoluble vitamins, vitamin A, vitamin E, vitamin F, vitamin D, mono-, di-, and tri-terpenoids, beta-ionol, cedrol, and their derivatives, water insoluble amino acids, tyrosine, tryptamine, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, particulate materials, pigment materials, natural colors, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and its salts, dihydroxyacetone, erythrulose, glyceraldehyde, tartaraldehyde, clove oil, menthol, camphor, eucalyptus oil, eugenol, menthyl lactate, witch hazel distillate, eicosene and vinyl pyrrolidone copolymers, iodopropyl butylcarbamate, a polysaccharide, an essential fatty acid, salicylate, glycyrrhetinic acid, carotenoides, ceramides and pseudo-ceramides, a lipid complex, oils in general of natural origin such shea butter, apricot oil, onagre oil, prunus oil, palm oil, monoi oil, HEPES; procysteine; O-octanoyl-6-D-maltose; the disodium salt of methylglycinediacetic acid, steroids such as diosgenin and derivatives of DHEA; DHEA or dehydroepiandrosterone and/or a precursor or chemical or biological derivative, N-ethyloxycarbonyl-4-para-aminophenol, bilberry extracts; phytohormones;

extracts of the yeast *Saccharomyces cerevisiae*; extracts of algae; extracts of soyabean, lupin, maize and/or pea; alverine and its salts, in particular alverine citrate, extract of butcher's broom and of horse chestnut, and mixtures thereof, a metalloproteinase inhibitor.

Further skin care and hair care active ingredients that are particularly useful in combination with the tri/tetrapeptide mixture can be found in SEDERMA commercial literature and on the website www.sederma.fr. (herewith incorporated in its entirety).

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

1) Sugar Amines (Amino Sugars)

The compositions of the present invention can comprise a sugar amine, which is also known as amino sugar. Sugar amine compounds useful in the present invention can include those described in PCT Publication WO 02/076423 and U.S. Pat. No. 6,159,485.

In one embodiment, the composition comprises from about 0.01% to about 15%, more preferably from about 0.1% to about 10%, and even more preferably from about 0.5% to about 5% by weight of the composition, of sugar amine.

Sugar amines can be synthetic or natural in origin and can be used as pure compounds or mixtures of compounds (e.g., extracts from natural sources or mixtures of synthetic materials). For example, glucosamine is generally found in many shellfish and can also be derived from fungal sources. As used herein, "sugar amine" includes isomers and tautomers of such and its salts (e.g., HCl salt) and is commercially available from Sigma Chemical Co.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine.

2) DHEA

The composition of the present invention may comprise DHEA or dehydroepiandrosterone and/or a precursor or biological or chemical derivative.

The term "DHEA precursor" concerns biological precursors of said DHEA which are likely to transform in DHEA during metabolism, as well as its chemical precursors which are likely to transform in DHEA by exogen chemical reaction. As non limiting examples of biological precursors, A5-pregnenolone, 17ahydroxy pregnenolone and 17ahydroxy pregnenolone sulfate can be cited. Also, as non limitating examples of chemical precursors, the sapogenins or their derivatives, such as diosgenine (or spriost-5-en-3-beta-ol), hecogenin, hecogenin acetate, smilagenin and sarsasapogenine, as well as the natural extracts containing them, in particular fenugrec and Disocorees extracts such as the wild igname roots or Wild Yam, can be cited.

The term "DHEA derivatives" comprises its chemical derivatives as well as its biological derivatives. As biological derivatives, A5-androstene-3,7-diol and A4-androstene-3,17-dione can be cited. DHEA salts, in particular hydrosoluble salts, like DHEA sulfate, can be cited as non limiting examples of chemical derivatives. Esters, such hydroxycarboxylic acid or DHEA esters disclosed for example in U.S. Pat. No. 5,736,537, or other esters such DHEA salicilate, acetate, valerate (or nheptanoate) and enanthate can also be cited. Derivatives of DHEA (DHEA carbamates, DHEA 2-hydroxy malonate, DHEA amino acid esters) disclosed in FR 00/03846 in the name of the Applicant can be cited. This list is obviously not exhaustive.

3) Metalloproteinase Inhibitors

The term "metalloproteinase inhibitor" relates to all molecule and/or plant or bacterial extract having a inhibitory activity on at least one of the metalloproteinases expressed or synthetized by or in the skin. The article of Y. HEROUY and al., European Journal of Dermatology, n 3, vol. 10, Avril-Mai 2000 discloses metalloproteinases (pp. 173-180). The family of the metalloproteinases is formed of several well-defined groups on the basis of their resemblance regarding structure and substrate specificity (Woessner J. F., Faseb Journal, vol. 5,1991, 2145). Among these groups, there are collagenases able to degrade fibrillar collagens (MMP-1 or interstitial collagenase, MMP-8 or neutrophil collagenase, MMP-13 or collagenase 3, MMP-18 or collagenase 4), gelatinases degrading type IV collagen or other denatured collagen form (MMP-2 or A gelatinase (72 kDa), MMP-9 or B gelatinase (92 kDa)), stromelysines (MMP-3 or stromelysine 1, MMP-10 or stromelysine 2, MMP-11 or stromelysine 3) whose broad spectrum of activity targets proteins of the extracellular matrix such as glycoproteins (fibronectin, laminin), proteoglycans etc., matrilysine (MMP-7), metalloelastase (MMP-12) or also the membrane metalloproteinases (MMP-14, MMP-15, MMP-16 et MMP-17). Metalloproteinases (MMPs) are proteases that use a metal, mostly zinc coordinated to 3 cysteine residues and to a methionine in their active site and that degrade macromolecular components of the extracellular matrix and of basal layers at neutral pH (collagen, elastin, etc . . . ) . . . . This group of enzymes is inactivated by metal chelators.

The principal activity regulators of MMPs are the tissue inhibitors of metalloproteinases or TIMPs such TIMP-1, TIMP-2, TIMP-3 and TIMP-4 (Woessner J. F., Faseb Journal, 1991). Furthermore, the MMPs expression is also regulated by growth factors, cytokines, oncogenes products (ras, jun), or also matrix constituents.

The term "metalloproteinase inhibitors>>according to the present invention means all molecule able to reduce the MMPs activity regarding the gene expression (transcription and translation) or regarding the activation of the zymogene form of MMPs, or else regarding the local control of active forms.

Furthermore, the metalloproteinase inhibitors according to the present invention can also be MMP-1 inhibitors of natural or synthetic origin. The terms "natural origin" or "synthetic origin" mean both a metalloproteinase inhibitor at a pure state or in solution at different concentrations, but natural inhibitors are obtained from different extraction methods of a natural origin term element (for example the lycopene) whereas the inhibitors of synthetic origin are all obtained via chemical synthesis.

4) Vitamin B3 Compounds

The compositions of the present invention can include a vitamin B3 compound. Vitamin B3 compounds are particularly useful for regulating skin conditions, as described in U.S. Pat. No. 5,939,082. In one embodiment, the composition comprises from about 0.001% to about 50%, more preferably from about 0.01% to about 20%, even more preferably from about 0.05% to about 10%, and still more preferably from about 0.1% to about 7%, even more preferably from about 0.5% to about 5%, by weight of the composition, of the vitamin B3 compound.

As used herein, "vitamin B3 compound" means a compound having the formula:

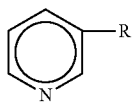

wherein R is —CONH2 (i.e., niacinamide), —COOH (i.e., nicotinic acid) or —CH2OH (i.e., nicotinyl alcohol); derivatives thereof; and salts of any of the foregoing.

Exemplary derivatives of the foregoing vitamin B3 compounds include nicotinic acid esters, including non-vasodilating esters of nicotinic acid (e.g., tocopherol nicotinate, myristyl nicotinate), nicotinyl amino acids, nicotinyl alcohol esters of carboxylic acids, nicotinic acid N-oxide and niacinamide N-oxide.

Suitable esters of nicotinic acid include nicotinic acid esters of C1-C22, preferably C1-C16, more preferably C1-C6 alcohols. Non-vasodilating esters of nicotinic acid include tocopherol nicotinate and inositol hexanicotinate; tocopherol nicotinate is preferred.

Other derivatives of the vitamin B3 compound are derivatives of niacinamide resulting from substitution of one or more of the amide group hydrogens. Specific examples of such derivatives include nicotinuric acid (C8H8N2O3) and nicotinyl hydroxamic acid (C6H6N2O2).

Exemplary nicotinyl alcohol esters include nicotinyl alcohol esters of the carboxylic acids salicylic acid, acetic acid, glycolic acid, palmitic acid and the like. Other non-limiting examples of vitamin B3 compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl)urea, 2-mercaptonicotinic acid, nicomol, and niaprazine.

Examples of the above vitamin B3 compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin B3 compounds may be used herein. Preferred vitamin B3 compounds are niacinamide and tocopherol nicotinate. Niacinamide is more preferred.

When used, salts, derivatives, and salt derivatives of niacinamide are preferably those having substantially the same efficacy as niacinamide.

Salts of the vitamin B3 compound are also useful herein. Nonlimiting examples of salts of the vitamin B3 compound useful herein include organic or inorganic salts, such as inorganic salts with anionic inorganic species (e.g., chloride, bromide, iodide, carbonate, preferably chloride), and organic carboxylic acid salts (including mono-, di- and tri-C1-C18 carboxylic acid salts, e.g., acetate, salicylate, glycolate, lactate, malate, citrate, preferably monocarboxylic acid salts such as acetate). These and other salts of the vitamin B3 compound can be readily prepared by the skilled artisan ("The Reaction of L-Ascorbic and D-Isoascorbic Acid with Nicotinic Acid and Its Amide", J. Organic Chemistry, Vol. 14, 22-26 (1949)).

The vitamin B3 compound may be included as the substantially pure material, or as an extract obtained by suitable physical and/or chemical isolation from natural (e.g., plant) sources. The vitamin B3 compound is preferably substantially pure, more preferably essentially pure.

5) Dehydroacetic Acid (DHA)

The composition of this invention can include dehydroacetic acid, having the structure:

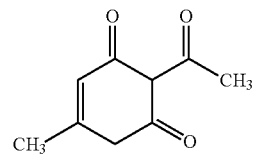

or pharmaceutically acceptable salts, derivatives or tautomers thereof. The technical name for dehydroacetic acid is 3-Acetyl-6-methyl-2H-pyran-2,4(3H)-dione and can be commercially purchased from Lonza.

Pharmaceutically acceptable salts include alkali metal salts, such as sodium and potassium; alkaline earth metal salts, such as calcium and magnesium; non-toxic heavy metal salts; ammonium salts; and trialkylammonium salts, such astrimethylammonium and triethylammonium. Sodium, potassium, and ammonium salts of dehydroacetic acid are preferred. Highly preferred is sodium dehydroacetate which can be purchased from Tri-K, as Tristat SDHA™. Derivatives of dehydroacetic acid include, but are not limited to, any compounds wherein the CH3 groups are individually or in combination replaced by amides, esters, amino groups, alkyls, and alcohol esters. Tautomers of dehydroacetic acid can be described as having the chemical formula C8H8O4 and generally having the structure above.

In one embodiment, the compositions of the present invention can comprise from about 0.001% to about 25% by weight of the composition, preferably from about 0.01% to about 10%, more preferably from about 0.05% to about 5%, and even more preferably from about 0.1% to about 1%, of dehydroacetic acid or pharmaceutically acceptable salts, derivatives or tautomers thereof.

6) Phytosterol

The compositions of the present invention can comprise a phytosterol. For example, one or more phytosterols can be selected from the group consisting of β-sitosterol, campesterol, brassicasterol, Δ5-avennasterol, lupenol, α-spinasterol, stigmasterol, their derivatives, analogs, and combinations thereof. More preferably, the phytosterol is selected from the group consisting of β-sitosterol, campesterol, brassicasterol, stigmasterol, their derivatives, and combinations thereof. More preferably, the phytosterol is stigmasterol.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers and tautomers of such and is commercially available from Aldrich Chemical Company, Sigma Chemical Company, and Cognis.

In one embodiment, the composition of the present invention comprises from about 0.0001% to about 25%, more preferably from about 0.001% to about 15%, even more preferably from about 0.01% to about 10%, still more preferably from about 0.1% to about 5%, and even more preferably from about 0.2% to about 2% phytosterol, by weight of the composition.

7) Salicylic Acid Compound

The compositions of the present invention may comprise a salicylic acid compound, its esters, its salts, or combinations thereof. In one embodiment of the compositions of the present invention, the salicylic acid compound preferably comprises from about 0.0001% to about 25%, more preferably from about 0.001% to about 15%, even more preferably from about 0.01% to about 10%, still more preferably from about 0.1% to about 5%, and even more preferably from about 0.2% to about 2%, by weight of the composition, of salicylic acid.

8) Hexamidine

The compositions of the present invention can include hexamidine compounds, its salts, and derivatives. In one embodiment, the hexamidine comprises from about 0.0001% to about 25%, more preferably from about 0.001% to about 10%, more preferably from about 0.01% to about 5%, and even more preferably from about 0.02% to about 2.5% by weight of the composition.

As used herein, hexamidine derivatives include any isomers and tautomers of hexamidine compounds including but not limited to organic acids and mineral acids, for example sulfonic acid, carboxylic acid, etc. Preferably, the hexamidine compounds include hexamidine diisethionate, commercially available as Eleastab® HP100 from Laboratoires Serobiologiques.

9) Dialkanoyl Hydroxyproline Compounds

The compositions of the present invention can comprise one or more dialkanoyl hydroxyproline compounds and their salts and derivatives.

In one embodiment, the dialkanoyl hydroxyproline compounds preferably comprise from about 0.01% to about 10%, more preferably from about 0.1% to about 5%, even more preferably from about 0.1% to about 2% by weight of the composition Suitable derivatives include but are not limited to esters, for example fatty esters, including, but not limited to tripalmitoyl hydroxyproline and dipalmityl acetyl hydroxyproline. A particularly useful compound is dipalmitoyl hydroxyproline. As used herein, dipalmitoyl hydroxyproline includes any isomers and tautomers of such and is commercially available under the tradename Sepilift DPHP® from Seppic, Inc. Further discussion of dipalmitoyl hydroxyproline appears in PCT Publication WO 93/23028. Preferably, the dipalmitoyl hydroxyproline is the triethanolamine salt of dipalmitoyl hydroxyproline.

10) Flavonoids.

The compositions of the present invention can comprise a flavonoid compound. Flavonoids are broadly disclosed in U.S. Pat. No. 5,686,082. As used herein, "flavonoid" means unsubstituted flavonoid or substituted flavonoid (i.e. mono-substituted flavonoid, or/and di-substituted flavonoid, or/and tri-substituted flavonoid). Examples of flavonoids particularly suitable for use in the present invention are one or more flavones, one or more flavanones, one or more isoflavones, one or more coumarins, one or more chromones, one or more dicoumarols, one or more chromanones, one or more chromanols, isomers (e.g., cis/trans isomers) thereof, and mixtures thereof.

Preferred for use herein are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy) and other plant sources of such mixtures (e.g., red clover), and mixtures thereof. Also preferred are favanones such as hesperitin, hesperidin, and mixtures thereof.

Flavonoid compounds useful herein are commercially available from a number of sources, e.g., Indofine Chemical Company, Inc., Steraloids, Inc., and Aldrich Chemical Company, Inc. Suitable flavonoïdes are commercially available called Sterocare® offered by SEDERMA and described in WO 99/18927.

In one embodiment, the herein described flavonoid compounds comprise from about 0.01% to about 20%, more preferably from about 0.1% to about 10%, and even more preferably from about 0.5% to about 5%, by weight of the composition.

11) N-Acyl Amino Acid Compound

The topical compositions of the present invention can comprise one or more N-acyl amino acid compounds. The amino acid can be one of any of the amino acids known in the art. The N-acyl amino acid compounds of the present invention can correspond to the formula:

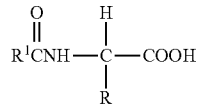

wherein R can be a hydrogen, alkyl (substituted or unsubstituted, branched or straight chain), or a combination of alkyl and aromatic groups.

Preferably, the N-acyl amino acid compound is selected from the group consisting of N-acyl Phenylalanine, N-acyl Tyrosine, their isomers, their salts, and derivatives thereof. The amino acid can be the D or L isomer or a mixture thereof.

Among the broad class of N-acyl Phenylalanine derivatives, particularly useful is N-undecylenoyl-L-phenylalanine commercially available under the tradename Sepiwhite® from SEPPIC.

In one embodiment, of the present invention, the N-acyl amino acid preferably comprises from about 0.0001% to about 25%, more preferably from about 0.001% to about 10%, more preferably from about 0.01% to about 5%, and even more preferably from about 0.02% to about 2.5% by weight of the composition.

12) Retinoid

The compositions of this invention can comprise a retinoid, preferably in a safe and effective amount such that the resultant composition is safe and effective for regulating keratinous tissue condition, preferably for regulating visible and/or tactile discontinuities in keratinous tissue (e.g., regulating signs of skin aging). The compositions can comprise from about 0.001% to about 10%, more preferably from about 0.005% to about 2%, even more preferably from about 0.01% to about 1%, still more preferably from about 0.01% to about 0.5%, by weight of the composition, of the retinoid. The optimum concentration used in a composition will depend on the specific retinoid selected since their potency can vary considerably.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably selected from retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), or mixtures thereof. More preferably the retinoid is a retinoid other than retinoic acid. These compounds are well known in the art and are commercially available from a number of sources, e.g., Sigma Chemical Company, and Boehringer Mannheim. Other retinoids which are useful herein are described in U.S. Pat. Nos. 4,677,120, 4,885,311, 5,049,584, 5,124,356, and Reissue 34,075. Other suitable retinoids can include tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 642-(4,4-dimethylthiochroman-6-yl)-ethynyl]nicotinate). Preferred retinoids include retinol, retinyl palmitate, retinyl acetate, retinyl propionate, retinal and combinations thereof. More preferred is retinyl propionate, used most preferably from about 0.1% to about 0.3%.

The retinoid may be included as the substantially pure material, or as an extract obtained by suitable physical and/or chemical isolation from natural (e.g., plant) sources. The retinoid is preferably substantially pure, more preferably essentially pure.

13) Optional Peptide

The composition of the present invention can comprise an additional peptide. Suitable peptides can include, but are not limited to, di-, tri-, tetra-, penta-, and hexa-peptides and derivatives thereof. In one embodiment, the composition comprises from about $1\times10^{-7}$% to about 20%, more preferably from about $1\times10^{-6}$% to about 10%, even more preferably from about $1\times10^{-5}$% to about 5%, by weight of additional peptide.

As used herein, "peptide" refers to peptides containing ten or fewer amino acids and their derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides.

Suitable dipeptides for use herein include but are not limited to Carnosine (beta-Ala-His), Tyr-Arg, Val-Trp (WO 0164178), Asn-Phe, Asp-Phe. Suitable tripeptides for use herein include, but are not limited to Arg-Lys-Arg (Peptide CK), His-Gly-Gly. Gly-His-Lys, Gly-Gly-His, Gly-His-Gy, Lys-Phe-Lys. Suitable tetrapeptides for use herein include but are not limited to, Peptide E, Arg-Ser-Arg-Lys (SEQ ID NO 25), Gly-Gln-Pro-Arg (SEQ ID NO 26). Suitable pentapeptides include, but are not limited to Lys-Thr-Thr-Lys-Ser (SEQ ID NO 24). Suitable hexapeptides include but are not limited to Val-Gly-Val-Ala-Pro-Gly (SEQ ID NO 27) and such as those disclosed in FR 2854897 and US 2004/0120918.

Other suitable peptides for use herein include, but are not limited to lipophilic derivatives of peptides, preferably palmitoyl derivatives, and metal complexes of the aforementioned (e.g., copper complex of the tripeptide His-Gly-Gly). Preferred dipeptide derivatives include N-Palmitoyl-beta-Ala-His, N-Acetyl-Tyr-Arg-hexadecylester (CAL-MOSENSINE™ from SEDERMA, France, WO 9807744, U.S. Pat. No. 6,372,717). Preferred tripeptide derivatives include N-Palmitoyl-Gly-Lys-His, (Pal-GKH from SEDERMA, France, WO 0040611), a copper derivative of His-Gly-Gly sold commercially as lamin, from Sigma, lipospondin (N-Elaidoyl-Lys-Phe-Lys) and its analogs of conservative substitution, N-Acetyl-Arg-Lys-Arg-NH2 (Peptide CK+), N-Biot-Gly-His-Lys (N-Biot-GHK from SEDERMA, WO0058347) and derivatives thereof. Suitable tetrapeptide derivatives for use herein include, but are not limited to N-palmitoyl-Gly-Gln-Pro-Arg (SEQ ID NO 26) (from SEDERMA, France), suitable pentapeptide derivatives for use herein include, but are not limited to N-Palmitoyl-Lys-Thr-Thr-Lys-Ser (SEQ ID NO 24) (available as MATRIXYL™ from SEDERMA, France, WO 0015188 and U.S. Pat. No. 6,620,419) N-Palmitoyl-Tyr-Gly-Gly-Phe-X with X Met or Leu (SEQ ID NO 28) or mixtures thereof. Suitable hexapeptide derivatives for use herein include, but are not limited to N-Palmitoyl-Val-Gly-Val-Ala-Pro-Gly (SEQ ID NO 27) and derivatives thereof.

The preferred compositions commercially available containing a tripeptide or a derivative include Biopeptide-CL™ by SEDERMA (WO0143701), Maxilip™ by SEDERMA (WO 0143701), Biobustyl™ by SEDERMA. The compositions commercially available preferred sources of tetrapeptides include RIGIN™ (WO0043417), EYELISS™ (WO03068141), MATRIXYL™ RELOADED, and MATRIXYL3000™ which contain between 50 and 500 ppm of palmitoyl-Gly-Gln-Pro-Arg (SEQ ID NO 26), and carrier, proposed by SEDERMA, France (US2004/0132667).

14) Ascorbates and Other Vitamins

The compositions of the present invention may comprise one or more vitamins, such as ascorbates (e.g., vitamin C, vitamin C derivatives, ascorbic acid, ascorbyl glucoside, ascorbyl palmitate, magnesium ascorbyl phosphate, sodium ascorbyl phosphate). Such vitamins can include, but are not limited to, vitamin B, vitamin B derivatives, vitamin B1 to vitamin B12 and theirs derivatives, vitamin K, vitamin K derivatives, vitamin H vitamin D, vitamin D derivatives, vitamin E, vitamin E derivatives, and provitamins thereof, such as panthenol and mixtures thereof. The vitamin compounds may be included as the substantially pure material, or as an extract obtained by suitable physical and/or chemical isolation from natural (e.g., plant) sources. In one embodiment, when vitamin compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the vitamin compound.

15) Particulate Material

The compositions of the present invention can comprise one or more particulate materials. Non limiting examples of particulate materials useful in the present invention include colored and uncolored pigments, interference pigments, inorganic powders, organic powders, composite powders, optical brightener particles, and combinations thereof. These particulates can, for instance, be platelet shaped, spherical, elongated or needle-shaped, or irregularly shaped, surface coated or uncoated, porous or non-porous, charged or uncharged, and can be added to the current compositions as a powder or as a pre-dispersion. In one embodiment, particulate materials are present in the composition in levels of from about 0.01% to about 20%, more preferably from about 0.05% to about 10%, still more preferably from about 0.1% to about 5%, by weight of the composition. There are no specific limitations as to the pigment, colorant or filler powders used in the composition.

Particulate materials useful herein can include, but are not limited to, bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, aluminum oxide, silicone resin, barium sulfate, calcium carbonate, cellulose acetate, PTFE, polymethyl methacrylate, starch, modified starches such as aluminum starch octenyl succinate, silk, glass, and mixtures thereof. Preferred organic powders/fillers include, but are not limited, to polymeric particles chosen from the methylsilsesquioxane resin microspheres such as, for example, those sold by Toshiba silicone under the name Tospearl 145A™, microspheres of polymethylmethacrylates such as those sold by Seppic under the name Micropearl M 100™, the spherical particles of crosslinked polydimethylsiloxanes, especially such as those sold by Dow Corning Toray Silicone under the name Trefil E 506C™ or Trefil E 505C™, spherical particles of polyamide and more specifically Nylon 12, especially such as those sold by Atochem under the name Orgasol 2002D Nat C05™, polystyrene microspheres such as for example those sold by Dyno Particles under the name Dynospheres™, ethylene acrylate copolymer sold by Kobo under the name Flo-Bead EA209™, PTFE, polypropylene, aluminium starch ocetenylsuccinate such as those sold by National Starch under the name Dry Ho™, microspheres of polyethylene such as those sold by Equistar under the name of Microthene FN510-00™, silicone resin, polymethylsilsesquioxane silicone polymer, platelet shaped powder made from L-lauroyl lysine, and mixtures thereof.

Also useful herein are interference pigments. The most common examples of interference pigments are micas layered with about 50-300 nm films of TiO2, Fe2O3, silica, tin oxide, and/or Cr2O3. Useful intereference pigments are available commercially from a wide variety of suppliers, for example, Rona (Timiron™ and Dichrona™), Presperse (Flonac™), Englehard (Duochrome™), Kobo (SK-45-R™ and SK-45-G™), BASF (Sicopearls™) and Eckart (e.g. Prestige Silk Red™).

Other pigments useful in the present invention can provide color primarily through selective absorption of specific wavelengths of visible light, and include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or ZrO2, are commercially available from a number of sources. One example of a suitable particulate material contains the material available from U.S. Cosmetics (TRONOX™ TiO2 series, SAT-T CR837™, a rutile TiO2).

The pigments/powders of the current invention can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobic treatments being preferred.

16) Sunscreen Actives

The compositions of the subject invention may optionally contain a sunscreen active. As used herein, "sunscreen active" includes both sunscreen agents and physical sunblocks. Suitable sunscreen actives may be organic or inorganic.

A wide variety of conventional organic or inorganic sunscreen actives are suitable for use herein. In one embodiment, the composition comprises from about 0.1% to about 20%, more typically from about 0.5% to about 10% by weight of the composition, of the sun screen active. Exact amounts will vary depending upon the sunscreen chosen and the desired Sun Protection Factor (SPF).

As examples of organic screening agents which are active in UV-A and/or UV-B, there may be mentioned in particular those designated below by their CTFA name:

para-aminobenzoic acid derivatives: PABA, Ethyl PABA, Ethyl Dihydroxypropyl PABA, Ethylhexyl Dimethyl PABA sold in particular under the trademark ESCALOL 507™ by ISP, Glyceryl PABA, PEG-25 PABA sold under the trademark UVINUL P25™ by BASF, salicyclic derivatives: Homosalate sold under the trademark EUSOLEX HMS™ by RONA/EM INDUSTRIES, Ethylhexyl Salicylate sold under the trademark NEO HELIOPAN OS™ by HAARMANN and REIMER, Dipropyleneglycol Salicylate sold under the trademark DIPSAL™ by SCHER, TEA Salicylate, sold under the trademark NEO HELIOPAN TS™ by HAARMANN and REIMER, dibenzoylmethane derivatives: Butyl Methoxydibenzoylmethane sold in particular under the trademark PARSOL 1789™ by HOFFMANN LA ROCHE, Isopropyl Dibenzolylmethane, cinnamic derivatives: Ethylhexyl Methoxycinnamate sold in particular under the trademark PARSOL MCX™ by HOFFMANN LA ROCHE, Isopropyl Methoxy Cinnamate, Isoamyl Methoxy Cinnamate sold under the trademark NEO HELIOPAN E 1000™ by HAARMANN and REIMER, Cinoxate, DEA Methoxycinnamate, Diisopropyl Methylcinnamate, Glyceryl Ethylhexanoate Dimethoxycinnamate, ββ'-diphenylacrylate derivatives: Octocrylene sold in particular under the trademark UVINUL N539™ by BASF, Etocrylene, sold in particular under the trademark UVINUL N35™ by BASF, benzophenone derivatives: Benzophenone-1 sold under the trademark UVINUL 400™ by BASF, Benzophenone-2 sold under the trademark UVINUL D50™ by BASF, Benzophenone-3 or Oxybenzone, sold under the trademark UVINUL M40™ by BASF, Benzophenone-4 sold under the trademark UVINUL MS40™ by BASF, Benzophenone-5, Benzophenone-6 sold under the trademark HELISORB 11™ by NORQUAY, Benzophenone-8 sold under the trademark SPECTRA-SORB UV-24™ by AMERICAN CYANAMID, Benzophenone-9 sold under the trademark UVINUL DS-49™ by BASF, Benzophenone-12, benzylidene camphor derivatives: 3-Benzylidene Camphor, 4-Methylbenzylidene Camphor sold under the trademark EUSOLEX 6300™ by MERCK, Benzylidene Camphor Sulphonic Acid, Camphor Benzalkonium Methosulphate, Terephthalylidene Dicamphor Sulphonic Acid, Polyacrylamidomethyl Benzylidene Camphor, phenylbenzimidazole derivatives: Phenylbenzimidazole Sulphonic Acid sold in particular under the trademark EUSOLEX 232™ by MERCK, Benzimidazilate sold under the trademark NEO HELIOPAN AP™ by HAARMANN and REIMER, triazine derivatives: Anisotriazine sold under the trademark TINOSORB S™ by CIBA GEIGY, Ethylhexyl triazones sold in particular under the trademark UVINUL T150™ by BASF, Diethylhexyl Butamido Triazone sold under the trademark UVASORB HEB™ by SIGMA 3V, phenylbenzotriazole derivatives: Drometrizole Trisiloxane sold under the trademark SILATRIZOLE™ by RHODIA CHIMIE, anthranilic derivatives: Menthyl anthranilate sold under the trademark NEO HELIOPAN MA™ by HAARMANN and REIMER, imidazoline derivatives: Ethylhexyl Dimethoxybenzylidene Dioxoimidazoline Propionate, benzalmalonate derivatives: Polyorganosiloxane with benzalmalonate functional groups sold under the trademark PARSOL SLX™ by HOFFMANN LA ROCHE, and mixtures thereof.

others: dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); uric and violuric acids; tannic acid and its derivatives (e.g., hexaethylether); (butyl carbotol) (6-propyl piperonyl)ether; hydroquinone;

The organic UV-screening agents which are more particularly preferred are chosen from the following compounds: Ethylhexyl Salicylate, Butyl Methoxydibenzoylmethane, Ethylhexyl Methoxycinnamate, Octocrylene, Phenylbenzimidazole Sulphonic Acid, Terephthalylidene Dicamphor Sulphonic, Benzophenone-3, Benzophenone-4, Benzophenone-5,4-Methylbenzylidene camphor, Benzimidazilate, Anisotriazine, Ethylhexyl triazone, Diethylhexyl Butamido Triazone, Methylene bis-Benzotriazolyl Tetramethylbutylphenol, Drometrizole Trisiloxane, and mixtures thereof.

Also preferred are the compositions described in U.S. Pat. No. 6,190,645 and in particular, sunscreen agents sold under the trademark INCROQUAT-UV-283™ manufactured by Croda, Inc.

The inorganic screening agents which may be used in the composition according to the invention are in particular nanopigments (mean size of the primary particles: generally between 5 nm and 100 nm, preferably between 10 nm and 50 nm) of coated or uncoated metal oxides such as for example nanopigments of titanium oxide (amorphous or crystallized in the form of rutile and/or anatase), iron, zinc, zirconium or cerium oxides and mixtures thereof. Coating agents are moreover alumina and/or aluminum stearate. Such nanopigments of metal oxides, coated or uncoated, are in particular described in EP-A-0-518,772 and EP-A-0-518,773.

When used herein, the inorganic sunscreens are present in the amount of from about 0.1% to about 20%, preferably from about 0.5% to about 10%, more preferably from about 1% to about 5%, by weight of the composition.

17) Anti-Cellulite Agents

The compositions of the present invention may also comprise an anti-cellulite agent. Suitable agents may include, but are not limited to, xanthine compounds (e.g., caffeine, theophylline, theobromine, and aminophylline In one embodiment, when anti-cellulite compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-cellulite compound.

Especially useful are combinations with the cellulite/slimming agents called Vexel™ (FR 2 654 619), Coaxel™ (FR 2 694 195), Cyclolipase™ (FR 2 733 149), Pleurimincyl™ and Lipocare™ (WO 98/43607) and Unislim™ (FR 0306063), all offered by SEDERMA.

18) Slimming, Toning or Draining Actives

The compositions can include one or more lipolytic agent selected among: phosphodiesterase inhibitors (e.g., xanthine derivatives), alpha-2 blockers compounds capable of blocking alpha-2 receptors at the adipocytes surface, beta-adrenergical agonists and antagonists (e.g. alverine and its organic or inorganic salts such as alverine citrate), agents inhibiting LDL and VLDL receptors synthesis, inhibitors of enzymes of fatty acid synthesis such as acetylCoA carboxylase, or fatty acid synthetase or cerulenine, compounds stimulating beta receptors and/or G proteins, glucose transport blockers such as serutine or rutine, neuropeptide Y (NPY) antagonists capable of blocking NPY receptors at the adipocytes surface, cAMP and its cosmetically acceptable derivatives, adenylate cyclase enzyme active agents such as forskolin, agents modifying fat acids transport, lipolytic peptides and lipolytic proteins, like peptides or proteins such as the peptides derived from the parathyroidal hormone, described in particular in the patents FR 2788058 and FR 2781231.

Others examples of usable lipolytic agents include botanical and marine extracts.

among plant extracts, there may more particularly be mentioned the extract of English ivy (*Hedera Helix*), of Chinese thorowax (*Bupleurum chinensis*), of arnica (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum Perforatum*), of butcher's-broom (*Ruscus aculeatus* L), of European meadowsweet (*Filipendula ulmaria* L), of big-flowered Jarva tea (*Orthosiphon Stamincus Benth*), of algae (*Fucus Vesiculosus*), of birch (*Betula alba*), of green tea, of cola nuts (*Cola Nipida*), of horse-chestnut, of bamboo, of spadeleaf (*Centella asiatica*), of heather, of fucus, of willow, of mouse-ear, extracts of escine, extracts of cangzhu, extracts of *chrysanthellum indicum*, extracts of the plants of the *Armeniacea* genus, *Atractylodis Platicodon, Sinnomenum, Pharbitidis, Flemingia*, extracts of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, extracts of *Guioa*, of *Davallia*, of *Terminalia*, of *Barringtonia*, of *Trema*, of antirobia, cecropia, argania, dioscoreae such as *Dioscorea opposita* or Mexican, as extracted of marine origin: extracts of algae or phytoplankton such as an extract of *Laminaria digitata*, diatoms, rhodysterol. All these extracts can of course to be taken in mixtures.

The compositions according to the invention can also contain in addition one or more additional active selected among: agents acting on the microcirculation (vasculoprotectors or vasodilators) such as the natural flavonoides, ruscogenines, esculosides, escine, nicotinates, heperidine methyl chalcone, butcher's-broom, essential oils of lavender or rosemary, the extracts of *Ammi visnaga*; anti-glycation agents such as extracts of *Centella asiatica* and *Siegesbeckia*, silicium, amadorine, ergothioneine and its derivatives, hydroxystilbenes and their derivatives (e.g. resveratrol), vegetable extracts of the family of Ericaceae, in particular bilberry extracts (*Vaccinium angustifollium*), vitamin C and its derivatives, retionol and its derivatives.

19) Butylated Hydroxytoluene (BHT) and Butylated Hydroxyanisole (BHA)

The topical compositions of the present invention may comprise BHT or BHA.

In one embodiment, BHT and/or BHA comprises from about 0.0001% to about 20% by weight of the composition, more preferably from about 0.001% to about 10%, even more preferably from about 0.01% to about 5%, and still more preferably from about 0.1% to about 0.5%.

20) Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

21) Desquamation Actives/Keratolytic Actives

A desquamating/keratolytic active may be added to the compositions of the present invention. In one embodiment, the composition comprises from about 0.01% to about 10%, preferably from about 0.1% to about 5%, more preferably from about 0.5% to about 2%, by weight of the composition, of a desquamating/keratolytic active.

Examples of useful keratolytic and/or desquamating agents include urea, salicylic acid and alkyl derivatives thereof, saturated and unsaturated monocarboxylic acids, saturated and unsaturated bicarboxylic acids, tricarboxylic acids, alpha hydroxyacids and beta hydroxyacids of monocarboxylic acids, alpha hydroxyacids and beta hydroxyacids of bicarboxylic acids, alpha hydroxyacids and beta hydroxyacids of tricarboxylic acids, ketoacids, alpha ketoacids, beta ketoacids, of the polycarboxylic acids, of the polyhydroxy monocarboxylic acids, of the polyhydroxy bicarboxylic acids, of the polyhydroxy tricarboxylic acids.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyheptanoic acid; 2-hydroxyoctanoic acid; 2hydroxynonanoic acid; 2-hydroxydecanoic acid; 2-hydroxyundecanoic acid; 2-hydroxydodecanoic acid (alpha-hydroxylauric acid); 2-hydroxytetradecanoic acid (alpha-hydroxymyristic acid); 2-hydroxyhexadecanoic acid (alpha-hydroxypalmitic acid); 2-hydroxyoctadecanoic acid (alpha-hydroxystearic acid); 2-hydroxyeicosanoic acid (alpha-hydroxyarachidonic acid); 2-phenyl 2-hydroxyethanoic acid (mandelic acid); 2,2-diphenyl 2-hydroxyethanoic acid (benzilic acid); 3-phenyl 2-hydroxypropanoic acid (phenyl lactic acid); 2-phenyl 2-methyl 2-hydroxyethanoic acid (atrolactic acid); 2-(4'-hydroxyphenyl) 2-hydroxyethanoic acid; 2-(4'-chlorophenyl 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3'-(2-hydroxyphenyl) 2-hydroxypropanoic acid; 3-(4'-hydroxyphenyl) 2-hydroxypropanoic acid; and 2-(3',4' dihydroxyphenyl), and 2-hydroxyethanoic acid, 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Preferred keratolytic agents are selected from the group comprising glycolic acid, tartaric acid, salicylic acid, citric acid, lactic acid, pyruvic acid, gluconic acid, glucuronic acid, malic acid, mandelic acid, oxalic acid, malonic acid, succinic acid, acetic acid, phenol, resorcine, retinoic acid, adapalene, trichloroacetic acid, 5-fluoro uracil, azelaic acid. Keratolytic agents are also the salts, esters, possible cis or trans forms, racemic mixtures and/or the relative dextrorotatory or levorotatory forms of the above listed compounds. Such substances can be used singularly or in associations with each other.

Other keratolytic agents suitable for use herein can include enzymatic exfoliant based on a protease called Keratoline™ and offered by Sederma.

One desquamation system that is suitable for use herein comprises salicylic acid and zwitterionic surfactants and is described in U.S. Pat. No. 5,652,228. Another desquamation system that is suitable for use herein contains sulfhydryl compounds and zwitterionic surfactants and is described in U.S. Pat. No. 5,681,852. Zwitterionic surfactants such as those described in this referenced patent can also be useful as desquamatory agents herein, with cetyl betaine being particularly preferred.

22) Anti-Acne Actives

The compositions of the present invention can comprise one or more anti-acne actives. Examples of useful anti-acne actives include resorcinol, sulfur, erythromycin, salicylic acid, benzoyl peroxide, dehydroacetic acid and zinc. Further examples of suitable anti-acne actives are described in U.S. Pat. No. 5,607,980. Especially useful are combinations with the anti-acne ingredient called Ac.net™ offered by SEDERMA (WO 03/028692 A2).

In one embodiment, when anti-acne compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-acne compound.

23) Anti-Wrinkle Actives/Anti-Atrophy Actives

The compositions of the present invention can comprise a one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol, hydroxy acids (e.g., alpha-hydroxy acids such as lactic acid and glycolic acid or beta-hydroxy acids such as salicylic acid and salicylic acid derivatives such as the octanoyl derivative, lactobionic acid), keto acids (e.g., pyruvic acid), phytic acid, ascorbic acid (vitamin), stilbenes, cinnamates, resveratrol, kinetin, zeatin, dimethylaminoethanol, peptides from natural sources (e.g., soy peptides), and salts of sugar acids (e.g., Mn gluconate, Zn gluconate), lipoic acid; lysophosphatidic acid, skin peel agents (e.g., phenol and the like), vitamin B3 compounds and retinoids and othervitamin B compounds (e.g., thiamine (vitamin B1), pantothenic acid (vitamin B5), riboflavin (vitamin B2), and their derivatives and salts (e.g., HCL salts or calcium salts). Especially useful are combinations with the wrinkle agents called Dermolectine™ and Sterocare™ offered by SEDERMA (WO99/18927).

In one embodiment, when anti-wrinkle/anti-atrophy compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-wrinkle/anti-atrophy compound.

24) Anti-Oxidants/Radical Scavengers

The compositions of the present invention can include an anti-oxidant/radical scavenger. In one embodiment, the composition comprises from about 0.01% to about 10%, more preferably from about 0.1% to about 5%, of an anti-oxidant/radical scavenger.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, amines (e.g., N,N-diethylhydroxylamine, amino-guanidine), nordihydroguaiaretic acid, bioflavonoids, sulfhydryl compounds (e.g., glutathione), dihydroxy fumaric acid and its salts, lycine pidolate, arginine pilolate, amino acids, silymarin, lysine, 1-methionine, proline, superoxide dismutase, sorbic acids and its salts, lipoic acid, olive extracts, tea extracts, polyphenols such as proanthocyanidine from pine bark, carotenoids, curcumin compounds such as tetrahydrocurcumin, OCTA (L-2-oxo-4-thiazolidine carboxylic acid), glutathione, melanin, rosemary extracts and grape skin/seed extracts may be used. Preferred anti-oxidants/radical scavengers can be selected from esters of tocopherol, more preferably tocopherol acetate and tocopherol sorbate (U.S. Pat. No. 4,847,071)

25) Humectants, Moisturizers and Conditioning Agents

The compositions of the present invention can contain a safe and effective amount of a conditioning agent selected from, for example, humectants, moisturizers, and skin conditioners. A variety of these materials can be employed and in one embodiment can be present at a level of from about 0.01% to about 20%, more preferably from about 0.1% to about 10%, and still more preferably from about 0.5% to about 7%, by weight of the composition. These materials can include, but are not limited to, guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, glycerol, hexanetriol, butanetriol, propylene glycol, butylene glycol, hexylene glycol and the like, polyethylene glycols, sugars (e.g., melibiose), starches, sugar and starch derivatives (e.g., alkoxylated glucose, fructose, glucosamine), hyaluronic acid, lactamide monoethanolamine, acetamide monoethanolamine, panthenol, allantoin, petroleum and mixtures thereof. Also useful herein are the propoxylated glycerols described in U.S. Pat. No. 4,976,953.

Also useful are various C1-C30 monoesters and polyesters of sugars and related materials. These esters are derived from a sugar or polyol moiety and one or more carboxylic acid moieties.

Preferably, the conditioning agent is selected from urea, guanidine, sucrose polyester, panthenol, dexpanthenol, allantoin, glycerol, and combinations thereof.

Humectants can be selected from the group consisting of polyhydric alcohols, water soluble alkoxylated nonionic polymers, and mixtures thereof. Polyhydric alcohols useful herein include polyhydroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

26) Active Oxygen Generation Inhibitors

The compositions of the present invention may also comprise a an active oxygen generation inhibitor selected from the group comprising quercetin, rutin, taxifolin, kaempferol, myricetin, curcumin, resveratrol, arecoline, apigenin, wogonin, luteolin, tectorigenin, and a mixture thereof.

This active oxygen generation inhibitor may be contained in an amount of about 0.001% to about 5%, more preferably in an amount of about 0.01% to about 3%%, by weight of the composition.

27) Chelators

The compositions of the present invention may also comprise a chelator or chelating agent. As used herein, "chelator" or "chelating agent" means an active agent capable of removing a metal ion from a system by forming a complex so that the metal ion cannot readily participate in or catalyze oxygen radical formation. In one embodiment, a chelating agent is added to a composition of the present invention, preferably from about 0.00001% to about 10%, more preferably from about 0.001% to about 5%, by weight of the composition. Exemplary chelators that are useful herein include those that are disclosed in U.S. Pat. No. 5,487,884, WO 91/16035 and WO 91/16034. Examples of chelating agents include N-hydroxysuccinimide, EDTA, NTA, deferoxamine, hydroxamic acids and their salts, phytic acid, phytate, gluconic acid and its salts, transferrine, lactoferrin; furildioxime and derivatives thereof.

28) Anti-Inflammatory Agents

An anti-inflammatory agent may be added to the compositions of the present invention. In one embodiment, an anti-inflammatory agent is added at a level of from about 0.01% to about 10%, preferably from about 0.5% to about 5%, by weight of the composition. The exact amount of anti-inflammatory agent to be used in the compositions will depend on the particular anti-inflammatory agent utilized since such agents vary widely in potency Steroidal anti-inflammatory agents can include, but are not limited to, corticosteroids such as hydrocortisone. In addition, nonsteroidal anti-inflammatory agents can be useful herein. The varieties of compounds encompassed by this group are well known to those skilled in the art. Specific non-steroidal anti-inflammatory agents that can be useful in the composition of the present invention include, but are not limited to, oxicams such as piroxicam, salicylates such as aspirin; acetic acid derivatives, such as felbinac, fenamates, such as etofenamate, flufenamic, mefenamic, meclofenamic, acids; propionic acid derivatives, such as ibuprofen, naproxen, pyrazoles, and mixtures thereof. Mixtures of these non-steroidal anti-inflammatory agents may also be employed, as well as the dermatologically acceptable salts and esters of these agents.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly

*Rubia Cordifolia*), and Guggal (extracted from plants in the genus *Commiphora*, particularly *Commiphora Mukul*), kola extract, chamomile, red clover extract, *Piper* methysticum extract (Kava Kava™ from SEDERMA (FR 2 771 002 and WO 99/25369), *Bacopa monieri* extract (Bacocalmine™ from SEDERMA, WO 99/40897) and sea whip extract, may be used. Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include C2-C24 saturated or unsaturated esters of the acids, preferably C10-C24, more preferably C16-C24. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred. Additional anti inflammatory agents include diosgenol, saponines, sapogenines, lignanes, triterpenes saponosides and genines.

29) Tanning Actives

The compositions of the present invention can comprise a tanning active. In one embodiment, the composition comprises from about 0.1% to about 20%, more preferably from about 2% to about 7%, and even more preferably from about 3% to about 6%, by weight of the composition, of a tanning active. A preferred tanning active is dihydroxyacetone, which is also known as DHA or 1,3-dihydroxy-2-propanone. Especially useful are combinations with the tanning agents called Tyr-ol™ and Tyr-excel™ offered by SEDERMA and described in Fr 2 702 766 and WO 03/017966 respectively.

30) Skin Whitening or Lightening Agents

The compositions of the present invention may contain a skin lightening agent. When used, the compositions preferably contain from about 0.01% to about 10%, more preferably from about 0.02% to about 5%, also preferably from about 0.05% to about 2%, by weight of the composition, of a skin lightening agent. Suitable skin lightening agents include those known in the art, including kojic acid, arbutin, tranexamic acid, ascorbic acid and derivatives thereof (e.g., magnesium ascorbyl phosphate or sodium ascorbyl phosphate, ascorbyl glucoside and the like), and extracts (e.g., mulberry extract, placental extract). Skin lightening agents suitable for use herein also include those described in WO95/34280, PCT/US95/07432, and co-pending U.S. Ser. No. 08/390,152. Especially useful are combinations with the skin lightening agents called Melaclear™, Etioline™, Melaslow™ and Lumiskin™ offered by SEDERMA and described respectively in FR 2 732 215, WO 98/05299, WO 02/15871 and PCT/FR 03/02400. Other skin lightening materials suitable for use herein can include Actiwhite® (Cognis), Emblica® (Rona), Azeloglicina™ (Sinerga) and Sepiwhite® (Seppic). A preferred skin lightening agent is ascorbyl glucoside.

31) Antimicrobial, Antibacterial and Antifungal Actives

The compositions of the present invention can comprise one or more anti-fungal or anti-microbial actives. A safe and effective amount of an antimicrobial or antifungal active can be added to the present compositions. In one embodiment, the composition comprises from about 0.001% to about 10%, preferably from about 0.01% to about 5%, and more preferably from about 0.05% to about 2%, by weight of the composition, of an antimicrobial or antifungal active.

Suitable anti-microbial actives include coal tar, sulfur, whitfield's ointment, castellani's paint, aluminum chloride, gentian violet, octopirox (piroctone olamine), 3,4,4'-trichlorocarbanilide (trichlosan), triclocarban, ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50™, Elestab HP-100™, azelaic acid, lyticase, iodopropynyl butylcarbamate (IPBC), isothiazalinones such as octyl isothiazolinone and azoles, and combinations thereof. Preferred anti-microbials include itraconazole, ketoconazole, selenium sulphide and coal tar. In one embodiment, one or more anti-fungal or anti-microbial active is combined with an anti-dandruff active selected from polyvalent metal salts of pyrithione.

a) Azoles

Azole anti-microbials include imidazoles such as benzimidazole, benzothiazole, bifonazole, butoconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein are ketoconazole and climb azole.

b) Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5 c) Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

d) Additional Anti-Microbial Actives

Additional anti-microbial actives of the present invention may include one or more keratolytic agents such as salicylic acid, extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.

Preferred examples of actives useful herein include those selected from the group consisting of benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, phytic acid, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, miconazole, ketoconazole, neomycin sulfate, and mixtures thereof.

Especially useful are combinations with the ingredient range called OSMOCIDE™ offered by SEDERMA (WO 97/05856).

32) Thickening Agents (Including Thickeners and Gelling Agents)

The compositions of the present invention can comprise one or more thickening agents. In one embodiment, a thickening agent is present at a level of from about 0.05% to about 10%, preferably from about 0.1% to about 5%, and more preferably from about 0.25% to about 4%, by weight of the composition. Nonlimiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. Nos. 5,087,445, 4,509,949, 2,798,053, and in CTFA International Cosmetic Ingredient Dictionary, Tenth Edition, 2004.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Godrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1™, and Pemulen TR-2™, from B.F. Goodrich. In other words, examples of carboxylic acid polymer thickeners useful herein are those selected from carbomers, acrylates/C10-C30 alkyl acrylate crosspolymers, and mixtures thereof.

b) Crosslinked Polyacrylate Polymers

The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. Nos. 5,100,660, 4,849,484, 4,835,206, 4,628,078, 4,599,379 and EP228868.

c) Polyacrylamide Polymers

The compositions of the present invention can optionally contain polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the Tradename Sepigel 305™ from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan™ SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties and may be used in concentration ranges between 1 and 99%, most advantageously between 5 and 15%.

d) Polysaccharides

A wide variety of polysaccharides can be useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™ CS11 from Michel Mercier Products Inc.

e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

33) Antiperspirant Actives

Antiperspirant actives may also be included in the compositions of the present invention. Suitable antiperspirant actives include astringent metallic salts, especially the inorganic and organic salts of aluminum zirconium and zinc, as well as mixtures thereof. Particularly preferred are the aluminum containing and/or zirconium-containing materials or salts, such as aluminum halides, aluminum chlorohydrate, aluminum hydroxyhalides, zirconyl oxyhalides, zirconyl hydroxyhalides, and mixtures thereof. In one embodiment, when antiperspirant actives are present in the compositions of the instant invention, the compositions comprise from about 0.01% to about 50%, more preferably from about 0.1% to about 40%, and still more preferably from about 1% to about 30%, by weight of the composition, of the antiperspirant compound.

34) Detersive Surfactants

The compositions of the present invention can include detersive surfactant from about 1% to about 90%, more preferably from about 5% to about 10%. The detersive surfactant component can be included to provide cleaning performance to the composition. The detersive surfactant component in turn can comprise anionic detersive surfactant, zwitterionic or amphoteric detersive surfactant, or a combination thereof.

Suitable anionic detersive surfactant components for use in the composition herein include those which are known for use in hair care or other personal care cleansing compositions. When included, the concentration of the anionic surfactant component in the composition can preferably be sufficient to provide the desired cleaning and lather performance, and generally can range from about 5% to about 50%, preferably from about 8% to about 30%, more preferably from about 10% to about 25%, even more preferably from about 12% to about 22%.

Preferred anionic surfactants suitable for use in the compositions are the alkyl and alkyl ether sulfates. Other suitable anionic detersive surfactants are the water-soluble salts of organic, sulfuric acid reaction products, alkoyl isethionates, sodium or potassium salts of fatty acid amides of methyl tauride, olefin sulfonates, beta-alkyloxy alkane sulfonates.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%. Non limiting examples of suitable zwitterionic or amphoteric surfactants are described in U.S. Pat. Nos. 5,104,646 and 5,106,609.

Amphoteric detersive surfactants include derivatives of aliphatic secondary and tertiary amines.

The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072, 2,438,091 and 2,528,378.

35) Cationic, Anionic and Amphoteric Polymers

The compositions of the present invention can comprise polymers which may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic When included, concentrations of the cationic polymer in the composition can typically range from about 0.05% to about 3%, preferably from about 0.075% to about 2.0%, more preferably from about 0.1% to about 1.0 a) Cationic Polymers

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate. Non limiting examples of such polymers are described in the CTFA.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyltriethylammonium bromide; amine derivatives of methacrylic acid or amine derivatives of methacrylamide derived from methacrylic acid or methacrylamide and a dialkylalkanolamine having C1-C6 alkyl groups such as dimethylaminoethyl (meth)acrylate, diethylaminoethyl (meth)acrylate, dimethylaminopropyl (meth)acrylate, or dimethylaminopropyl (meth)acrylamide Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. A non limiting example is polymethyacrylamidopropyl trimonium chloride, available under the trade name Polycare 133™, from Rhone-Poulenc.

Other suitable cationic polymers for use in the composition include polysaccharide polymers, such as cationic cellulose derivatives and cationic starch derivatives.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200™.

Other suitable cationic polymers include cationic guar gum derivatives, such as guar hydroxypropyltrimonium chloride, specific examples of which include the Jaguar™ series commercially available from Rhone-Poulenc Incorporated and the N-Hance™ series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

b) Anionic Polymers

Examples of anionic polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

c) Amphoteric Monomers

Examples of the amphoteric monomers include zwitterionized derivatives of the aforementioned amine derivatives of (meth)acrylic acids or the amine derivatives of (meth)acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth) acrylamide, as discussed above, modified with propanesultone.

36) Nonionic Polymers

The compositions herein can comprise nonionic polymers. For instance, polyalkylene glycols having a molecular weight of more than about 1000 can be used. Preferred polyethylene glycol polymers can include PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Examples of nonionic monomers are acrylic or methacrylic acid esters of C1-C24 alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene, chlorostyrene, vinyl esters such as vinyl acetate, vinyl chloride, vinylidene chloride, acrylonitrile, alpha-methylstyrene, t-butylstyrene, butadiene, cyclohexadiene, ethylene, propylene, vinyl toluene, alkoxyalkyl (meth)acrylate, methoxy ethyl (meth)acrylate, butoxyethyl (meth)acrylate, allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, n-butyl methacrylate, isobutyl methacrylate, 2-ethylhexyl methacrylate, methyl methacrylate, t-butylacrylate, t-butylmethacrylate, and mixtures thereof 37) Hair Conditioning Agents Conditioning agents include any material which is used to give a particular conditioning benefit to keratinous tissue. For instance, in hair treatment compositions, suitable conditioning agents include those which deliver one or more benefits relating to shine, softness, combability, antistatic properties, wet-handling, damage, manageability, body, and greasiness. Conditioning agents useful in the compositions of the present invention can comprise a water insoluble, water dispersible, non-volatile liquid that forms emulsified, liquid particles. Suitable conditioning agents for use in the composition include those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

When included, the concentration of the conditioning agent in the composition can be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

a) Silicones

The conditioning agent of the compositions of the present invention is preferably an insoluble silicone conditioning agent. The silicone conditioning agent particles may comprise volatile silicone, non-volatile silicone, or combinations thereof. Non-volatile silicon conditioning agents are preferred. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609.

Background material on silicones including sections discussing silicone fluids, gums, and resins, as well as manufacture of silicones, are found in Encyclopedia of Polymer Science and Engineering, vol. 15, 2d ed., pp 204-308, John Wiley & Sons, Inc. (1989).

b) Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

c) Amino and Cationic Silicones

Cationic silicone fluids suitable for use in the compositions of the present invention include, but are not limited to, the polymer known as "trimethylsilylamodimethicone".

Other silicone cationic polymers which may be used in the compositions of the present invention may be UCARE SILICONE ALE 56™, available from Union Carbide.

d) Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, Chemistry and Technology of Silicones, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

e) High Refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. Nos. 2,826,551, 3,964,500, 4,364,837, GB849433, and Silicon Compounds, Petrarch Systems, Inc. (1984).

f) Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

38) Organic Conditioning Oils

Compositions of the present invention may also comprise organic conditioning oil. In one embodiment, from about 0.05% to about 20%, preferably from about 0.08% to about 1.5%, more preferably from about 0.1% to about 1%, of at least one organic conditioning oil is included as a conditioning agent, either alone or in combination with other conditioning agents, such as the silicones (described herein).

a) Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about C12 to about C19. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation, hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

b) Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of C4 to about C14 olefenic monomers, preferably from about C6 to about C12.

Preferred non-limiting examples of olefenic monomers for use in preparing the polyolefin liquids herein include ethylene, propylene, 1-butene, 1-pentene, 1-hexene to 1-hexadecenes, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

c) Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of C4 to C8 dicarboxylic acids (e.g. C1 to C22 esters, preferably C1 to C6, of succinic acid, glutaric acid, and adipic acid). Specific non-limiting examples of di- and tri-alkyl and alkenyl esters of carboxylic acids include isocetyl stearoyl stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as C10 to C22 carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters.

Specific non-limiting examples of suitable synthetic fatty esters for use in the compositions of the present invention include: P-43™ (C8-C10 triester of trimethylolpropane), MCP-684™ (tetraester of 3,3 diethanol-1,5 pentadiol), MCP 121™ (C8-C10 diester of adipic acid), all of which are available from Mobil Chemical Company.

39) Anti-Dandruff Actives

The compositions of the present invention may also contain an anti-dandruff agent. Suitable, non-limiting examples of anti-dandruff particulates include: pyridinethione salts, azoles, selenium sulfide, particulate sulfur, and mixtures thereof. Preferred are pyridinethione salts, especially 1-hydroxy-2-pyridinethione salts. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"). Pyridinethione anti-dandruff agents are described, for example, in U.S. Pat. Nos. 2,809,971; 3,236,733; 3,761,418; 4,345,080; 4,323, 683; 4,379,753 and 4,470,982.

40) Humectant

The compositions of the present invention may contain a humectant. Humectants can be selected from the group consisting of polyhydric alcohols, water soluble alkoxylated nonionic polymers, and mixtures thereof. Humectants, when used herein, are preferably used at levels of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

41) Suspending Agent

The compositions of the present invention may further comprise a suspending agent, preferably at concentrations effective for suspending water-insoluble material in dispersed form in the compositions or for modifying the viscosity of the composition. Such concentrations can preferably range from about 0.1% to about 10%, more preferably from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, nitro cellulose, sodium carboxymethyl cellulose, crystalline cellulose, cellulose powder, polyvinylpyrrolidone, polyvinyl alcohol, guar gum, hydroxypropyl guar gum, arabia gum, galactan, carob gum, pectin, agar, quince seed (*Cyclonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid. Actives aforementioned as thickening agents can also be used herein as suspending agents.

Commercially available viscosity modifiers highly useful herein include Carbomers with tradenames Carbopol 934™, Carbopol 940™, Carbopol 950™, Carbopol 980™, and Carbopol 981™, all available from B. F. Goodrich Company, acrylates/steareth-20 methacrylate copolymer with tradename ACRYSOL 22™ available from Rohm and Hass, non-oxynyl hydroxyethylcellulose with tradename AMERCELL POLYMER HM-1500™ available from Amerchol, methylcellulose with tradename BENECEL™, hydroxyethyl cellulose with tradename NATROSOL™, hydroxypropyl cellulose with tradename KLUCEL™, cetyl hydroxyethyl cellulose with tradename POLYSURF 67™, all supplied by Hercules, ethylene oxide and/or propylene oxide based polymers with tradenames CARBOWAX PEGs™, POLYOX WASRs™, and UCON FLUIDS™, all supplied by Amerchol.

Other optional suspending agents include crystalline suspending agents which can be categorized as acyl derivatives, long chain amine oxides, long chain acyl derivatives and mixtures thereof. These suspending agents are described in U.S. Pat. No. 4,741,855. These preferred suspending agents include ethylene glycol esters of fatty acids, alkanol amides of fatty acids, long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® available from Rheox, Inc Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

42) Terpene Alcohol

The compositions of the present invention may comprise a terpene alcohol or combinations of terpene alcohols. As used herein, "terpene alcohol" refers to organic compounds composed of two or more 5-carbon isoprene units [CH2=C(CH3)-CH=CH2] with a terminal hydroxyl group. Preferably, the composition can comprise from about 0.001% to about 50%, preferably from about 0.01% to about 20%, more preferably from about 0.1% to about 15%, even more preferably from about 0.1% to about 10%, still more preferably from about 0.5% to about 5%, and still more preferably from about 1% to about 5%, by weight of the composition, of the terpene alcohol.

Examples of terpene alcohols that can be useful herein include farnesol, derivatives of farnesol, isomers of farnesol, geraniol, derivatives of geraniol, isomers of geraniol, phytantriol, derivatives of phytantriol, isomers of phytantriol, and mixtures thereof. A preferred terpene alcohol for use herein is farnesol.

a) Farnesol and Derivatives Thereof.

Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names Farnesol™ (a mixture of isomers from Dragoco) and Trans-trans-farnesol™ (Sigma Chemical Company). A suitable derivative of farnesol is farnesyl acetate which is commercially available from Aldrich Chemical Company.

b) Geraniol and Derivatives Thereof.

Geraniol is the common name for the chemical known as 3,7-dimethyl-2,6-octadien-1-ol. As used herein, "geraniol" includes isomers and tautomers of such. Geraniol is commercially available from Aldrich Chemical Company. Suitable derivatives of geraniol include geranyl acetate, geranylgeraniol, geranyl pyrophosphate, and geranylgeranyl pyrophosphate, all of which are commercially available from Sigma Chemical Company. For example, geraniol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

c) Phytantriol and Derivatives Thereof.

Phytantriol is the common name for the chemical known as 3,7,11,15, tetramethylhexadecane-1,2,3,-triol. Phytantriol is commercially available from BASF. For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

43) Enzymes, Enzyme Inhibitors and Enzyme Activators (Coenzymes)

The compositions of the present invention may contain a safe and effective amount of one or more enzymes, enzyme inhibitors or enzyme activators (coenzymes). Examples of enzymes are lipases, proteases, catalase, superoxide-dismutase, amylases, glucuronidases, peroxidases, in particular glutathione peroxidase or lactoperoxidase, ceramidases, hyaluronidases. All of these enzymes may be obtained by extraction or by fermentation biotechnology processes. Examples of enzyme inhibitors include trypsin inhibitors, Bowmann Birk inhibitor, chymotrypsin inhibitors, botanical extracts with or without tannins, flavonoids, quercetin which inhibit enzymatic activity. Enzyme preparations can be found, for instance, in the product named VENUCEANE™ proposed by SEDERMA, France (WO 02/066668). Enzyme activators and coenzymes include Coenzyme A, coenzyme Q10 (ubiquinone), glycyrrhizidine, berberine, chrysine.

II CARRIER

The compositions of the present invention can comprise an orally or a dermatologically acceptable carrier, or injectible liquid, depending upon the desired product form.

A. Dermatologically Acceptable Carrier

The topical compositions of the present invention can also comprise a dermatologically acceptable carrier for the composition. In one embodiment, the carrier is present at a level of from about 50% to about 99.99%, preferably from about 60% to about 99.9%, more preferably from about 70% to about 98%, and even more preferably from about 80% to about 95%, by weight of the composition.

The carrier can be in a wide variety of forms. Non-limiting examples include simple solutions (water or oil based), emulsions, and solid forms (gels, sticks). For example, emulsion carriers can include, but are not limited to, oil-in-water, water-in-oil, water-in-silicone, water-in-oil-in-water, and oil-in-water-in-silicone emulsions.

Depending upon the desired product form, preferred carriers can comprise an emulsion such as oil-in-water emulsions (e.g., silicone in water) and water-in-oil emulsions, (e.g., water-in-silicone emulsions). As will be understood by the skilled artisan, a given component will distribute primarily into either the water or oil phase, depending on the water solubility/dispensability of the component in the composition. In one embodiment, oil-in-water emulsions are especially preferred.

Emulsions according to the present invention can contain an aqueous phase and a lipid or oil. Lipids and oils may be derived from animals, plants, or petroleum and may be natural or synthetic (i.e., man-made).

Preferred emulsions can also contain a humectant, such as glycerin. Emulsions can further comprise from about 0.1% to about 10%, more preferably from about 0.2% to about 5%, of an emulsifier, based on the weight of the composition. Emulsifiers may be nonionic, anionic or cationic. Suitable emulsifiers are disclosed in, for example, U.S. Pat. Nos. 3,755,560, 4,421,769, and McCutcheon's Detergents and Emulsifiers, North American Edition, pages 317-324 (1986). Suitable emulsions may have a wide range of viscosities, depending on the desired product form.

The compositions of the present invention can be in the form of pourable liquids (under ambient conditions). The compositions can therefore comprise an aqueous carrier, which is typically present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

The emulsion may also contain an anti-foaming agent to minimize foaming upon application to the keratinous tissue. Anti-foaming agents include high molecular weight silicones and other materials well known in the art for such use.

Preferred water-in-silicone and oil-in-water emulsions are described in greater detail below.

1) Water-in-Silicone Emulsion

Water-in-silicone emulsions contain a continuous silicone phase and a dispersed aqueous phase.

a) Continuous Silicone Phase

Preferred water-in-silicone emulsions of the present invention contain from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the active ingredients of the present invention. The continuous silicone phase of these preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid, Dow Corning® 225 fluid, and Dow Corning® 200 fluids Examples of suitable alkyl-substituted dimethicones include cetyl dimethicone and lauryl dimethicone.

Cyclic polyalkylsiloxanes suitable for use in the composition include commercially available cyclomethicones such as Dow Corning® 244 fluid, Dow Corning® 344 fluid, Dow Corning® 245 fluid and Dow Corning® 345 fluid.

Also useful are materials such as trimethylsiloxysilicate. A commercially available trimethylsiloxysilicate is sold as a mixture with dimethicone as Dow Corning® 593 fluid.

Dimethiconols are also suitable for use in the composition. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

b) Dispersed Aqueous Phase

The topical compositions of the present invention contain from about 30% to about 90%, more preferably from about 50% to about 85%, and still more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelants, gums, water-soluble or dispersible alcohols and polyols, buffers, preservatives, sunscreening agents, colorings, and the like.

The topical compositions of the present invention will typically contain from about 25% to about 90%, preferably from about 40% to about 80%, more preferably from about 60% to about 80%, water in the dispersed aqueous phase by weight of the composition.

c) Emulsifier for Dispersing the Aqueous Phase

The water-in-silicone emulsions of the present invention preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present invention, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename WS-08 (also available from Goldschmidt) Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

Dimethicone copolyol emulsifiers useful herein are described, for example, in U.S. Pat. No. 4,960,764, European Patent No. EP 330,369, Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, Detergents and Emulsifiers, North American Edition (1986), published by Allured Publishing Corporation; U.S. Pat. Nos. 5,011,681; 4,421,769; and 3,755,560

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

d) Silicone Elastomer

The compositions of the present invention also include from about 0.1% to about 30%, by weight of the composition, of a silicone elastomer component. Preferably, the composition includes from about 1% to about 30%, more preferably from about 2% to about 20%, by weight of the composition, of the silicone elastomer component.

Suitable for use herein are silicone elastomers, which can be emulsifying or non-emulsifying crosslinked siloxane elastomers or mixtures thereof. No specific restriction exists as to the type of curable organopolysiloxane composition that can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane and condensation-curing organopolysiloxane compositions which cure in the presence of an organotin compound or a titanate ester.

Addition reaction-curing organopolysiloxane compositions are preferred for their rapid curing rates and excellent uniformity of curing. A particularly preferred addition reaction-curing organopolysiloxane composition is prepared from: a) an organopolysiloxane having at least 2 lower alkenyl groups in each molecule; b) an organopolysiloxane having at least 2 silicon-bonded hydrogen atoms in each molecule; and c) a platinum-type catalyst.

The compositions of the present invention may include an emulsifying crosslinked organopolysiloxane elastomer, a non-emulsifying crosslinked organopolysiloxane elastomer, or a mixture thereof. The term "non-emulsifying," as used herein, defines crosslinked organopolysiloxane elastomers from which polyoxyalkylene units are absent. The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomers can notably be chosen from the crosslinked polymers described in U.S. Pat. Nos. 5,412,004, 5,837,793, and 5,811,487. In addition, an emulsifying elastomer comprised of dimethicone copolyol crosspolymer (and) dimethicone is available from Shin Etsu under the tradename KSG-21™.

Advantageously, the non-emulsifying elastomers are dimethicone/vinyl dimethicone crosspolymers. Such dimethicone/vinyl dimethicone crosspolymers are supplied by a variety of suppliers including Dow Corning (DC 9040™ and DC 9041™), General Electric (SFE 839™), Shin Etsu (KSG™-15,16,18 [dimethicone/phenyl vinyl dimethicone crosspolymer]), and Grant Industries (GRANSIL™ line of elastomers). Cross-linked organopolysiloxane elastomers useful in the present invention and processes for making them are further described in U.S. Pat. Nos. 4,970,252, 5,760,116 and 5,654,362.

Commercially available elastomers preferred for use herein are Dow Corning's 9040™ silicone elastomer blend, Shin Etsu's KSG-21™, and mixtures thereof.

e) Carrier for Silicone Elastomer

The topical compositions of the present invention may include from about 1% to about 80%, by weight of the composition, of a suitable carrier for the for the crosslinked organopolysiloxane elastomer component described above. The carrier, when combined with the cross-linked organopolysiloxane elastomer particles of the present invention, serves to suspend and swell the elastomer particles to provide an elastic, gel-like network or matrix. The carrier for the cross-linked siloxane elastomer is liquid under ambient conditions, and preferably has a low viscosity to provide for improved spreading on the skin.

Concentrations of the carrier in the cosmetic compositions of the present invention will vary primarily with the type and amount of carrier and the cross-linked siloxane elastomer employed. Preferred concentrations of the carrier are from about 5% to about 50%, more preferably from about 5% to about 40%, by weight of the composition.

The carrier for the cross-linked siloxane elastomer includes one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C., preferably from about 28° C. to about 100° C., preferably from about 28° C. to about 78° C. The term "volatile" as used herein refers to all materials that are not "non-volatile" as previously defined herein. The phrase "relatively polar" as used herein means more polar than another material in terms of solubility parameter; i.e., the higher the solubility parameter the more polar the liquid. The term "non-polar" typically means that the material has a solubility parameter below about 6.5 (cal/cm3>)05.

f) Non-Polar, Volatile Oils

The composition of the present invention may include non-polar, volatile oils. The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. Such non-polar, volatile oils are disclosed, for example, in Cosmetics, Science, and Technology, Vol. 1, 27-104 edited by Balsam and Sagarin, 1972. Examples of preferred non-polar, volatile hydrocarbons include polydecanes such as isododecane and isodecane (e.g., Permethyl-99A™ which is available from Presperse Inc.) and the C7-C8 through C12-C15 isoparaffins (such as the Isopar™ Series available from Exxon Chemicals). Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200™, Dow Corning 244™, Dow Corning 245™, Dow Corning 344™, and Dow Corning 345™, (commercially available from Dow Corning Corp.); SF-1204™ and SF-1202™ Silicone Fluids (commercially available from G.E. Silicones), GE 7207™ and 7158™ (commercially available from General Electric Co.); and SWS-03314™ (commercially available from SWS Silicones Corp.).

g) Relatively Polar, Non-Volatile Oils

The composition of the present invention may include relatively polar, non-volatile oils. The non-volatile oil is "relatively polar" as compared to the non-polar, volatile oil discussed above. Therefore, the non-volatile co-carrier is more polar (i.e., has a higher solubility parameter) than at least one of the non-polar, volatile oils. Relatively polar, non-volatile oils potentially useful in the present invention are disclosed, for example, in Cosmetics, Science, and Technology, Vol. 1, 27-104 edited by Balsam and Sagarin, 1972; U.S. Pat. Nos. 4,202,879 and 4,816,261. Relatively polar, non-volatile oils useful in the present invention are preferably selected from silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof.

h) Non-Polar, Non-Volatile Oils

In addition to the liquids discussed above, the carrier for the cross-linked siloxane elastomer may optionally include non-volatile, non-polar oils. Typical non-volatile, non-polar emollients are disclosed, for example, in Cosmetics, Science, and Technology, Vol. 1, 27-104 edited by Balsam and Sagarin, 1972; U.S. Pat. Nos. 4,202,879 and 4,816,261. The non-volatile oils useful in the present invention are essentially non-volatile polysiloxanes, paraffinic hydrocarbon oils, and mixtures thereof.

2) Oil-in-Water Emulsions

Other preferred topical carriers include oil-in-water emulsions, having a continuous aqueous phase and a hydrophobic, water-insoluble phase ("oil phase") dispersed therein. The "oil phase" can contain oil, silicone or mixtures thereof, and includes but is not limited to the oils and silicones described above in the section on water-in-oil emulsions. The distinction of whether the emulsion is characterized as an oil-in-water or silicone-in-water emulsions is a function of whether the oil phase is composed of primarily oil or silicone. The water phase of these emulsions consists primarily of water, but can also contain various other ingredients such as those water phase ingredients listed in the above section on water-in-oil emulsion. The preferred oil-in-water emulsions comprises from about 25% to about 98%, preferably from about 65% to about 95%, more preferably from about 70% to about 90% water by weight of the total composition.

In addition to a continuous water phase and dispersed oil or silicone phase, these oil-in-water compositions also comprise an emulsifier to stabilize the emulsion. Emulsifiers useful herein are well known in the art, and include nonionic, anionic, cationic, and amphoteric emulsifiers. Non-limiting examples of emulsifiers useful in the oil-in-water emulsions of this invention are given in McCutcheon's, Detergents and Emulsifiers, North American Edition (1986), U.S. Pat. Nos. 5,011,681, 4,421,769 and 3,755,560. Examples of suitable oil-in-water emulsion carriers are described in U.S. Pat. Nos. 5,073,371 and 5,073,372. An especially preferred oil-in-water emulsion, containing a structuring agent, hydrophilic surfactant and water, is described in detail hereinafter.

a) Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention contain from about 0.5% to about 20%, more preferably from about 1% to about 10%, even more preferably from about 1% to about 5%, by weight of the composition, of a structuring agent.

The preferred structuring agents of the present invention include stearic acid, palmitic acid, stearyl alcohol, cetyl alcohol, behenyl alcohol, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

b) Hydrophilic Surfactant

The preferred oil-in-water emulsions contain from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Preferred hydrophilic surfactants are selected from nonionic surfactants. Among the nonionic surfactants that are useful herein are those that can be broadly defined as condensation products of long chain alcohols, e.g. C8-30 alcohols, with sugar or starch polymers, i.e., glycosides. These compounds can be represented by the formula (S)n-O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS™ from Henkel) and lauryl polyglucoside (available as APG 600 CS™ and 625 CS™ from Henkel).

Other useful nonionic surfactants include the condensation products of alkylene oxides with fatty acids (i.e. alkylene oxide esters of fatty acids), the condensation products of alkylene oxides with 2 moles of fatty acids (i.e. alkylene oxide diesters of fatty acids), the condensation products of alkylene oxides with fatty alcohols (i.e. alkylene oxide ethers of fatty alcohols), the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants, An especially preferred surfactant corresponding to the above structure is coconut alkyl N-methyl glucoside amide. Processes for making compositions containing polyhydroxy fatty acid amides are disclosed, for example, U.S. Pat. Nos. 2,965,576; 2,703,798, and 1,985,424.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another group of non-ionic surfactants useful herein are fatty acid ester blends based on a mixture of sorbitan or sorbitol fatty acid ester and sucrose fatty acid ester, the fatty acid in each instance being preferably C8-C24, more preferably C10-C20. The preferred fatty acid ester emulsifier is a blend of sorbitan or sorbitol C16-C20 fatty acid ester with sucrose C10-C16 fatty acid ester, especially sorbitan stearate and sucrose cocoate. This is commercially available from ICI under the trade name Arlatone 2121™.

Other suitable surfactants useful herein include a wide variety of cationic, anionic, zwitterionic, and amphoteric surfactants such as are known in the art and discussed more fully below. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, especially dialkyl quaternary ammonium compounds, examples of which are described in U.S. Pat. Nos. 5,151,209; 5,151,210; 5,120,532; 4,387,090; 3,155,591; 3,929,678; 3,959,461; McCutcheon's, Detergents & Emulsifiers, (North American edition 1979) M.C. Publishing Co.; and Schwartz, et al., Surface Active Agents, Their Chemistry and Technology, New York: Interscience Publishers, 1949.

Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C30 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents.

A wide variety of anionic surfactants can also be useful herein. Nonlimiting examples of anionic surfactants include the alkoyl isethionates, and the alkyl and alkyl ether sulfates. The reaction products of fatty acids esterified with isethianonic acid and neutralized, i.e. the alkoyl isethionates typically have the formula RCO—OCH2CH2SO3M wherein R is alkyl or alkenyl of from about 10 to about 30 carbon atoms, and M is a water-soluble cation such as ammonium, sodium, potassium and triethanolamine. For example, the fatty acids are derived from coconut or palm kernel oil. Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof. Also suitable are salts of fatty acids, amids of methyl taurides. Other similar anionic surfactants are described in U.S. Pat. Nos. 2,486,921; 2,486,922 and 2,396,278.

The alkyl and alkyl ether sulfates typically have the respective formulae ROSO3M and RO(C2H4O)xSO3M, wherein R is alkyl or alkenyl of from about 10 to about 30 carbon atoms, x is from about 1 to about 10, and M is a water-soluble cation such as ammonium, alkanolamines such as triethanolamine, monovalent metals, such as sodium and potassium, and polyvalent metal cations such as magnesium and calcium. Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized Another suitable class of anionic surfactants are the water-soluble salts of the organic, sulfuric acid reaction products of the general formula:

R1-SO3-M wherein R1 is chosen from the group including a straight or branched chain, saturated aliphatic hydrocarbon radical having from about 8 to about 24, preferably about 10 to about 16, carbon atoms; and M is a cation described hereinbefore. Still other anionic synthetic surfactants include the class designated as succinamates, olefin sulfonates having about 12 to about 24 carbon atoms, and P-alkyloxy alkane sulfonates. Examples of these materials are sodium lauryl sulfate and ammonium lauryl sulfate. Other anionic surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid. Other suitable anionic surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the compositions is the beta-alkyloxy alkane sulfonate class. These surfactants conform to the formula

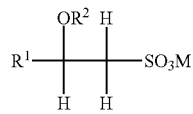

where R1 is a straight chain alkyl group having from about 6 to about 20 carbon atoms, R2 is a lower alkyl group having from about 1 to about 3 carbon atoms, preferably 1 carbon atom, and M is a water-soluble cation as described hereinbefore. Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH2)mCO2M]2 and RNH(CH2)mCO2M wherein m is from 1 to 4, R is a C8-C22 alkyl or alkenyl, and M is H, alkali metal, alkaline earth metal ammonium, or alkanolammonium. Preferred amphoteric surfactants for use in the present invention include cocoamphoacetate, cocoamphodiacetate, lauroamphoacetate, lauroamphodiacetate, and mixtures thereof. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072; N-higher alkyl aspartic acids such as those produced according to the teaching of U.S. Pat. No. 2,438,091; and the products sold under the trade name "Miranol" and described in U.S. Pat. No. 2,528,378. Other examples of useful amphoterics include phosphates, such as coamidopropyl PG-dimonium chloride phosphate (commercially available as Monaquat PTC™, from Mona Corp.).

Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP™ from Lonza Corp.), lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and amidobetaines and amidosulfobetaines (wherein the RCONH(CH2)3 radical is attached to the nitrogen atom of the betaine), oleyl betaine (available as amphoteric Velvetex OLB-50™ from Henkel), and cocamidopropyl betaine (available as Velvetex BK-35™ and BA-35™ from Henkel).

Other useful amphoteric and zwitterionic surfactants include the sultaines and hydroxysultaines such as cocamidopropyl hydroxysultaine (available as Mirataine CBS™ from Rhone-Poulenc), and the alkanoyl sarcosinates corresponding to the formula RCON(CH3)CH2CH2CO2M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

c) Water Emollient

The preferred oil-in-water emulsion contains from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) contains numerous examples of materials suitable as an emollient. A preferred emollient is glycerin. Glycerin is preferably used in an amount of from or about 0.001 to or about 30%, more preferably from or about 0.01 to or about 20%, still more preferably from or about 0.1 to or about 10%, e.g., 5%.

Lotions and creams according to the present invention generally contain a solution carrier system and one or more emollients. Lotions and creams typically contain from about 1% to about 50%, preferably from about 1% to about 20%, of emollient; from about 50% to about 90%, preferably from about 60% to about 80%, water; the actives and the additional skin care active (or actives) in the above described amounts. Creams are generally thicker than lotions due to higher levels of emollients or higher levels of thickeners.

Ointments of the present invention may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, Cosmetics, Science and Technology, 2nd Edition, Vol. 1, pp. 72-73 (1972), and/or an emollient. For example, an ointment may contain from about 2% to about 10% of an emollient; from about 0.1% to about 2% of a thickening agent as well as the active ingredient(s) and the additional ingredient(s) in the above described amounts.

Compositions of this invention useful for cleansing ("cleansers") can be formulated with a suitable carrier, e.g., as described above, and preferably comprise from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, for exemplary surfactants useful herein. Examples of a broad variety of additional surfactants useful herein are described in McCutcheon's Detergents and Emulsifiers, North American Edition (1986), published by Allured Publishing Corporation. The cleansing compositions can optionally contain, at their art-established levels, other materials which are conventionally used in cleansing compositions.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier and may include conventional ingredients such as oils, colorants, pigments, emollients, fragrances, waxes, stabilizers, and the like. Exemplary carriers and such other ingredients which are suitable for use herein are described, for example in PCT Application WO 96/33689, and U.K. Patent GB 2274585.

B. Orally Acceptable Carrier The compositions of the present invention can also comprise an orally acceptable carrier if they are to be ingested. Any suitable orally ingestible carrier or carrier form, as known in the art or otherwise, can be used. Non-limiting examples of oral personal care compositions can include, but are not limited to, tablets, pills, capsules, drinks, beverages, syrups, granules, powders, vitamins, supplements, health bars, candies, chews, and drops.

C. Injectible Liquid

The compositions of the present invention can also comprise a liquid that is acceptable for injection in and/or under the skin if the composition is to be injected. Any suitable acceptable liquid as known in the art or otherwise can be used.

III. COMPOSITION PREPARATION

The compositions of the present invention are generally prepared by conventional methods such as are known in the art of making topical and oral compositions and compositions for injection. Such methods can typically be conducted in one or more steps, with or without heating, cooling, and the like.

The physical form of the compositions according to the invention is not important: they may be in any galenic form such creams, lotions, milk or cream ointments, gels, emulsions, dispersions, solutions, suspensions, cleansers, foundations, anhydrous preparations (sticks, in particular lipbalm, body and bath oils), shower and bath gels, shampoos and scalp treatment lotions, cream or lotion for care of skin or hair, make-up removing lotions or creams, sun-screen lotions, milks or creams, artificial suntan lotions, creams or milks, pre-shave, shave or aftershave creams, foams, gels or lotions, make-up, lipsticks, mascaras or nail varnishes, skin "essences," serums, adhesive or absorbent materials, transdermal patches, or powders, emollient lotion, milk or cream, sprays, oils for the body and the bath, foundation tint bases, pomade, emulsion, colloid, compact or solid suspension, pencil, sprayable or brossable formulation, blush, rouge, eyeliner, lipliner, lip gloss, facial or body powder, mousse or styling gels, nail conditioner, lip balms, skin conditioners, moisturizers, hair sprays, soaps, body exfoliants, astringents, depilatories and permanent waving solutions, antidandruff formulations, anti-sweat and antiperspirant compositions, nose sprays and so on. These compositions can also be presented in the form of lipsticks intended to apply colour or to protect the lips from cracking, or of make-up products for the eyes or tints and tint bases for the face. Compositions in accordance with the invention include cosmetics, personal care products and pharmaceutical preparations. The present invention may also be applied on animal skin and/or appendages. One can also consider a composition in the shape of foam or in the form of compositions for aerosol also including a propellant agent under pressure.

Cosmetic compositions according to the invention may also be for orodental use, for example, toothpaste. In that case, the compositions may contain the usual adjuvants and additives for compositions for oral use and, in particular, surfactants, thickening agents, moisturizing agents, polishing agents such as silica, various active substances such as fluorides, particularly sodium fluoride, and, possibly, sweetening agents such as saccharin sodium.

The composition of the invention may be in the form of solution, dispersion, emulsion, paste, or powder, individually or as a premix or in vehicles individually or as a premix in vectors such as macro-, micro-, or nanocapsules, macro-, micro- or, nanospheres, liposomes, oleosomes or chylomicrons, macro-, micro-, or nanoparticles or macro-, micro or nanosponges, micro or nano emulsions or adsorbed on organic polymer powders, talcs, bentonites, or other inorganic or organic supports.

The peptides, peptidic compounds and the corresponding cosmetic compositions of the present invention may be used in any form whatsoever, in a form bound to or incorporated in or absorbed in or adsorbed on macro-, micro-, and nanoparticles, or macro-, micro-, and nanocapsules, for the treatment of textiles, natural or synthetic fibres, wools, and any materials that may be used for clothing or underwear for day or night intended to come into contact with the skin, handkerchiefs or cloths, to exert their cosmetic effect via this skin/textile contact and to permit continuous topical delivery.

IV. METHOD OF COSMETIC TREATMENT

The composition according to the invention can be applied locally onto areas of the face, neck, neckline, hands or body. One of the major advantages of the present invention is the possibility of being able to perform whenever necessary or desirable, "gentle", highly localised selective treatments using the topical method of application.

The present invention also concerns peptides or peptidic compounds for their application as a medicinal product and in particular for the preparation of a medicinal product intended to treat wrinkles and lines, and to increase skin elasticity and dermo-epidermal properties.

The present invention concerns the chemical, medical, cosmetics and skincare industries.

As an illustration of the invention, several cosmetic formulations will be described hereafter. These formulations are representative of but do not restrict the invention.

IV. METHOD OF COSMETIC OR DERMO-PHARMACEUTICAL TREATMENT

The present invention also concerns a cosmetic treatment process to improve the general state of the skin involving topical application of an effective amount of the composition as defined above to the skin. More specifically:
- to prevent and/or treat the signs of intrinsic and extrinsic skin ageing;
- to prevent and/or treat skin slackening and/or improve tone and/or firmness and/or elasticity of the skin;
- to prevent and/or treat skin atrophy and/or improve the density of the dermis and epidermis;
- to give or return volume to the dermis and epidermis;
- to prevent and/or treat skin dehydration;
- to prevent and/or treat skin roughness;
- to prevent and/or treat hair loss;
- to prevent and/or treat cellulite, to reduce expansion and/or prevent the development of adipose tissue within the hypodermis;
- to lighten and/or whiten the skin;
- to prevent and/or treat glycation of molecules in the skin;
- to prevent and/or treat acne;
- to prevent and/or treat degradation of the skin due to the effects of oxidation;
- to prevent and/or treat inflammatory states.

The composition according to the invention may be applied locally onto areas of the face, lips, neck, neckline, hands, feet or body. One of the major advantages of the present invention resides in the ability whenever necessary or desirable to be able to apply local selective "gentle" treatment through the topical, non-invasive method of application. In the case of anti-wrinkle use for example it may be applied very locally using a syringe or micro-canula.

It is also possible, however, to consider a composition containing the peptide or peptidic compound according to the invention intended to be injected subcutaneously.

According to other specific features the treatment process according to the invention with one or more other treatment processes targeting the skin such as luminotherapy or aromatherapy treatments.

According to the invention, devices with several compartments or kits may be proposed to apply the process described above which may include for example and non-restrictively, a first compartment containing a composition including the peptide or peptide compound, with a composition containing another active ingredient and/or excipient in a second compartment, the compositions contained in the said first and second compartments in this case being considered to be a combination composition for simultaneous, separate or stepwise use in time, particularly in one of the treatments defined above.

V. EXAMPLES

The following examples describe and demonstrate various aspects within the scope of the present invention. The examples are only given for illustrative purposes and should not be considered to be restrictive to this invention. Additionally for illustrative purposes several cosmetic formulations will be described. These formulations are representative of but do not restrict the invention.

Example 1

Example of Preparation of a Composition Containing Peptide Pal-KMO$_2$K-OH.2HCl Peptide Synthesis:

Peptide Pal-KMO$_2$K-OH.2HCl is prepared by solid phase peptide synthesis. The first lysine K is protected on the N-terminal part by a Fmoc protective group and on the side chain by a Boc protective group. The protected lysine (Fmoc-Lys(Boc)-OH) is attached to a solid support (Wang resin). After unprotecting the Fmoc group with piperidine, the second pre-protected amino acid (Fmoc-Methionine sulfone-OH) is bound in the presence of a binding agent (HBTU, HOBt for example). Once binding is complete a further piperidine unprotection step is performed and the 3$^{rd}$ protected amino acid (Fmoc-Lys(Boc)-OH) is bound. The unprotection step is repeated and the final binding with palmitic acid is performed. Finally the side groups are unprotected and the peptide is cleaved from the resin with trifluoroacetic acid (TFA) in the presence of "trapping" agents (TIS-H$_2$O).

Preparation of the Composition

Starting Products:
  pure peptide Pal KMO$_2$K-OH.2HCl synthesized by the synthetic process explained above;
  Excipients: mixture of fatty esters selected to form an oily matrix, for example intended to form a water-free composition for the subsequent formulation of water-free cosmetic compositions.

Operating Process:

Peptide Pal KMO$_2$K-OH.2HCl is combined with the excipient and stirred gently and heated until totally dissolved and clear.

Example 2

Example of Preparation of a Composition Containing Peptide Pal-KMO$_2$K-OH.2HCl and an Extract of *Portulaca pilosa*

Preparation of the Extract:
Starting Products:
  Active plant: *Portulaca pilosa*, ground whole plant;
  Excipient: fatty ester
Extraction Method:
  The ground plant is added to the fatty ester and the mixture is stirred for 30 minutes. It is then filtered and the extract is recovered.
Preparation of the Composition:
  The composition prepared in example 1 is added to the plant extract, stirring vigorously at room temperature until a micro emulsion (clear mixture) is formed. An oily liquid mixture is obtained after filtration. Typically, this composition may contain 0.05% peptide and 2% plant by weight compared to the total weight of the composition.

Example 3

Results of In Vitro Tests on Examples According to the Invention

Description of Tests
  ELISA Test on Normal Human Dermal Fibroblasts (NHF)
  This test examines the dermal molecules.
  Normal human dermal fibroblasts are cultured in multi-well plates. The cells either are or are not placed in contact with the test substances for 3 days. The culture supernatants are removed and the quantity of macromolecules present (collagen I, fibronectin, collagen IV and hyaluronic acid) is assayed by ELISA.
  ELISA Test on Human Keratinocytes (HK)
  This test examines epidermal molecules.
  Human keratinocytes are cultured in multi-well plates. The cells either are or are not placed in contact with the test substances for 3 days. The culture supernatants are removed and the quantity of macromolecules present (fibronectin, laminins and hyaluronic acid) is assayed by ELISA.
  Immunofluorescence (IMF) on Normal Human Dermal Fibroblasts (NHF)
  This test examines dermal molecules.
  Norman human fibroblasts are cultured in plates. The cells either are or are not placed in contact with the test substances for 35 days. The cell layers are then labeled with antibodies specifically recognizing collagen III. Photographs were used to reveal and quantify the synthesis of collagen III.
  The results shown below are statistically significant (the difference between the test substance and the placebo (or control) is statistically significant (Student "t" test)).
  Table 1 Showing % Difference in Collagen I in the Dermis Compared to the Control-ELISA Test on Dermal NHF.

|  | R | Peptide | α-aa | ppm | Collagen I in the dermis |
|---|---|---|---|---|---|
| Examples of peptides according to the invention | —(CH$_2$)$_2$—S—CH$_3$ | Pal-KMK-OH | Methionine | 4 | +21 |
|  |  |  |  | 6 | +63 |
|  |  |  |  | 8 | +64 |
|  | —(CH$_2$)$_2$—SO$_2$—CH$_3$ | Pal-KMO$_2$K-OH | Dioxidized Methionine | 4 | +188 |
|  |  |  |  | 6 | +187 |
|  | —CH$_2$—SH | Pal-KCK-OH | Cysteine | 4 | +145 |
|  |  |  |  | 6 | +133 |
|  | —(CH$_2$)$_2$—CONH$_2$ | Pal-KQK-OH | Glutamine | 5 | +82 |
|  | —CH$_2$—CONH$_2$ | Pal-KNK-OH | Asparagine | 5 | +55 |

-continued

|  | R | Peptide | α-aa | ppm | Collagen I in the dermis |
|---|---|---|---|---|---|
| Examples of peptides according to the prior art | —CH$_2$—OH<br>—CH$_3$ | Pal-KSK-OH<br>Pal-KAK-OH | Serine<br>Alanine | 4<br>4 | +46<br>+42 |

The peptides according to the invention produce a significant increase in collagen I synthesis in the dermis at concentrations of a few ppm: Pal-KMK-OH +63% at 6 ppm, Pal-KMO2K-OH +188% at only 4 ppm, Pal-KCK-OH +145% also at only 4 ppm, Pal-KQK-OH +82% at 5 ppm and Pal-KNK-OH +55% also at 5 ppm.

These results are better than those obtained with the two peptides from the prior art tested. At 4 ppm for example, Pal-KMO$_2$K-OH produces a +188% increase in collagen I in the dermis, Pal-KCK-OH +145% whereas the two peptides from the prior art produce increases of only 46% for Pal-KSK-OH and 42% for Pal-KAK-OH at 4 ppm.

Oxidizing the sulfur increases the rise in collagen I synthesis in the dermis: peptide Pal-KMO$_2$K-OH at 4 ppm displays a large increase of +188% compared to a 63% increase for unoxidized Pal-KMK-OH.

Table 2 Showing % Differences in Other Dermal Molecules Compared to the Control—ELISA Test on Dermal NHF.

|  | Peptide | ppm | Coll. I | Fibronectin | Coll. IV | Hyaluronic acid |
|---|---|---|---|---|---|---|
| Invention | Pal-KMO2K—OH | 4 | +188 | +42 | +27 | ≈0 |
|  |  | 6 | +187 | +109 | +97 | +55 |
|  | Pal-KCK—OH | 4 | +145 | +57 | −1 |  |
|  |  | 6 | +133 | +70 | +23 |  |
|  | Pal-KQK—OH | 5 | +82 | +35 |  |  |
| Prior art | Pal-KSK—OH | 4 | +46 | +26 | +1 |  |
|  | Pal-KAK—OH | 4 | +42 | +33 | −6 |  |

The results in table 2 show that the peptides according to the invention are able to significantly stimulate molecules other than collagen I: at 4 ppm, Pal-KMO$_2$K-OH stimulates collagen I, fibronectin and collagen IV synthesis at 6 ppm, Pal-KMO$_2$K-OH also stimulates synthesis of hyaluronic acid; Pal-KCK-OH also stimulates the synthesis of collagen I and fibronectin.

Conversely, the two peptides from the prior art tested show lesser increases in fibronectin and collagen IV synthesis.

Table 3 Showing % Differences in Collagen III in the Dermis Compared to the Control—IMF Tests on Dermal NHF.

|  | ppm peptide | Coll. III |
|---|---|---|
| Pal-KMO2K—OH | 5 | +104 |

This test shows that Pal-KMO$_2$K-OH stimulates the synthesis of collagen III in the dermis at a peptide concentration of 5 ppm.

Table 4 Showing % Differences in Other Epidermal Molecules Compared to the Control—ELISA and IMF Tests on Epidermal HK

|  | Ppm of peptide | Fibronectin | Hyaluronic acid | Laminins |
|---|---|---|---|---|
| Pal-KMO2K—OH | 4 | +35 | +139 | +30 |
|  | 5 | +65 | +172 | +66 |
|  | 6 | +159 | +290 | +172 |

In the epidermis, Pal-KMO$_2$K-OH is seen to potently stimulate the synthesis of fibronectin, hyaluronic acid and laminins Results are particularly impressive at 6 ppm.

Comparative Example
Pal-KMO$_2$K-OH/Pal-KMO$_2$K-OH +Extract of *Portulaca pilosa* Plant Table 5 Showing % Differences in Other Dermal Molecules Compared to the Control—ELISA and IMF Tests on Dermal NHF.

| Assay method | ppm peptide | ppm plant | Coll. I ELISA | Fibronectin ELISA | Coll. IV ELISA | Hyaluronic acid ELISA | Coll. III IMF |
|---|---|---|---|---|---|---|---|
| Pal-KMO2K—OH | 5 |  | +111 | +59 | +42 | ≈0 | +104 |
| Pal-KMO2K—OH + *Portulaca pilosa* | 5 | 20 | +116 | +73 | +84 | +32 | +223 |

These results show that in the dermis, the mixture Pal-KMO$_2$K-OH/*Portulaca pilosa* stimulates collagen I, III and IV, fibronectin and hyaluronic acid. Compared to peptide Pal-KMO$_2$K-OH alone at 5 ppm the mixture produces better stimulation of fibronectin, collagen III and IV and hyaluronic acid. The presence of the plant extract from *Portulaca pilosa* therefore provides a synergistic effect in the dermis.

Table 6 Showing % Differences in Hyaluronic Acid in the Epidermis Compared to the Control—ELISA and IMF Tests on Epidermal HK

|  | ppm peptide | ppm plant | Hyaluronic acid |
|---|---|---|---|
| Pal-KMO$_2$K—OH | 2 |  | +44 |
|  | 4 |  | +139 |
|  | 5 |  | +172 |
|  | 6 |  | +290 |
| Pal-KMO$_2$K—OH + | 2 | 8 | +62 |
| *Portulaca pilosa* | 4 | 16 | +191 |
|  | 5 | 20 | +224 |
|  | 6 | 24 | +301 |

Compared to peptide Pal-KMO$_2$K-OH alone, Pal-KMO$_2$K-OH/*portulaca pilosa* produces greater stimulation of hyaluronic acid. The presence of the plant extract from *portulaca pilosa* therefore provides a synergistic effect on the epidermis.

The results also specifically show that Pal-KMO$_2$K-OH is able to simultaneously stimulate the synthesis of a large number of dermal and epidermal extracellular matrix molecules:

in the dermal extracellular matrix: collagen I, III and IV, fibronectin and hyaluronic acid.

in the epidermal extracellular matrix: fibronectin, hyaluronic acid and laminins.

Table 7 Showing % Differences in Collagen I in the Dermis Compared to the Control for Dioxygenated Peptide Compounds According to the Immunostaining Method or to ELISA Test on Dermal NHF

|  | Collagen I in the dermis | | |
|---|---|---|---|
|  | ppm | Test 1 | Test 2 |
| Pal-MO2-K-OH | 2 |  | +270 |
|  | 4 |  | +457 |
|  | 6 |  | +226 |
| Pal-MO2-Ava-NH$_2$ | 2 |  | +375 |
|  | 4 |  | +582 |
|  | 6 |  | +461 |
| Pal-Ava-MO2-NH$_2$ | 2 |  | +495 |
|  | 4 |  | +667 |
|  | 6 |  | +557 |
| Pal-K-MO2-K-OH | 2 |  | +329 |
|  | 4 | +188 | +423 |
|  | 5 |  | +486 |
|  | 6 | +187 |  |
| Pal-MO2-T-K-F-OH (SEQ ID NO 29) | 2 |  | +218 |
|  | 4 | +111 | +456 |
|  | 6 | +148 | +520 |
| Pal-K-T-MO2-K-OH (SEQ ID NO 30) | 2 |  | +273 |
|  | 4 | +75 | +341 |
|  | 6 | +161 | +262 |
| Pal-K-F-MO2-K-OH (SEQ ID NO 31) | 4 | +80 |  |
|  | 6 | +81 |  |
| Pal-K-T-F-MO2-NH$_2$ (SEQ ID NO 32) | 2 |  | +267 |
|  | 4 | +106 | +420 |
|  | 6 | +121 | +400 |
| Pal-K-MO2-T-K-OH (SEQ ID NO 33) | 4 | +45 | +192 |
|  | 6 | +194 | +217 |
| Pal-K-MO2-F-K-OH (SEQ ID NO 34) | 4 | +91 |  |
| Pal-K-Ava-MO2-K-OH (SEQ ID NO 35) | 2 | +63 |  |
|  | 4 | +167 |  |
| Pal-K-MO2-Ava-K-OH (SEQ ID NO 36) | 2 | +75 |  |
| Peptides non oxygenated according to the invention | | | |
| Pal-K-M-K-OH | 4 | +21 |  |
|  | 6 | +63 |  |
| Pal-K-Ava-K-OH | 4 | +116 |  |
|  | 6 | +175 |  |
| Pal-K-T-F-K-OH (SEQ ID NO 57) | 4 | +82 |  |
|  | 6 | +103 |  |

The peptide compounds according to the invention containing a sulfur atom in an oxygenated form produce positives results on the synthesis of collagen I in the dermis.

Comparison examples are also given in the above table with existing peptides not containing oxygenated sulfur according to the invention: the activity of Pal-KMO2K-OH is greatly increased (from +21 to +188 at 4 ppm and from +63 to +187 at 6 ppm), the activity of Pal-MO2-T-F-K-OH is increased compared to Pal-K-T-F-K-OH (from +82 to +111 at 4 ppm and from +103 to +148 at 6 ppm), the activity of Pal-K-T-MO2-K-OH is increased compared to Pal-K-T-F-K-OH (+103 to +161 at 6 ppm), the activity of Pal-K-T-F-MO2-NH$_2$ is increased compared to Pal-K-T-F-K-OH (from +82 to +106 at 4 ppm and from +103 to +121 at 6 ppm), the activity of Pal-K-Ava-MO2-K-OH is increased compared to Pal-K-Ava-K-OH (from +116 to +167 at 4 ppm).

Example 3

Examples of Galenics

Example 3.1

Formulation of a Lip Balm

| Composition | INCI Name | 100 g |
|---|---|---|
| PHASE A | | |
| Crodamol SS | Caprylic/capric triglycerides | 5 g |
| Syncrowax HRC | Tribehenin | 10 g |
| Crodamol MM | Myristyl myristate | 10 g |
| Crodamol GTCC | Cetyl esters | 37 g |
| Castor Oil | *Ricinus communis* seed oil | 37 g |
| PHASE B | | |
| Peptide or peptidic compound according to the invention | | 1 g (i.e. 5 ppm of peptide) |

Protocol:

Weigh Phase A, melt at around 75° C. and mix. Weigh Phase B, add to Phase A at around 65° C. and homogenise. Pour the mixture into an appropriate container.

Properties.

A significant improvement in skin firmness and moisturising capacity is obtained with a fall in roughness (dry, chipped appearance of the lips and area around the lips), a significant increase in lip volume, particularly in the lower lip and in the density of the superficial dermis (the most damaged part during the ageing process). The lips are replumped, firmer and softer. The curve of the lips is more pronounced.

Example 3.2

Formulation of a Lipstick

| Composition | INCI Name | 100 g |
|---|---|---|
| PHASE A | | |
| Crill 6 | Sorbitan Stearate | 7 g |
| Seaton Castor oil | Castor oil | 0.1 g |
| Crodamol PTIS UK | Pentaerythrityl Tetraisostearate | 0.7 g |
| Syncrowax HRC | Tribehenin | |
| Syncrowax ERLC | C 18-36 Acid Glycol Ester | 3.0 g |
| Crodacol S 95 | Stearyl alcohol | 0.8 g |
| Crodacol C 90 | Cetyl alcohol | |
| Crodamol SS | Cetyl esters | 1.0 g |
| Syncrowax HGLC | C 18-36 Acid Triglyceride | 2.0 g |
| Prisorine 3700 | Polyglyceryl-3 diisostearate | 19.0 g |
| PHASE B | | |
| Phytessence Urucum | Caprylic/capric trigyceride & bixa Orellana seed Extract | 1.0 g |
| PHASE C | | |
| Composition containing 0.05% by weight of peptide or a peptidic compound according to the invention in an oily excipient | | 1.0 g (i.e. 5 ppm of peptide or peptidic compound) |
| Coviox T 70 | Tocopherol acetate | 0.1 g |
| PHASE D | | |
| Strawberry fragrance | Fragrance | 0.1 g |

Protocol:

Weigh Phase A, melt at around 90° C. and successively add Phases B, C and D, mixing, and then pour the product into the mould. Leave to cool to ambient temperature and then cool.

Properties:

This lipstick is particularly effective in moisturising, maintaining moisturisation and forming a protective barrier to preserve the moisturisation. The lips are also redensified, replumped and softer.

Example 3.3

Formulation of a Body Oil (Continuous Oil Phase on Silicone Base)

| Composition | INCI Name | 100 g |
|---|---|---|
| PHASE A | | |
| Sorbate | Potassium Sorbate | 0.1 g |
| MgSO4 | Magnesium sulphate | 0.7 g |
| PHASE B | | |
| ABIL E 90 | Cetyl PEG/PPG-10/1 Dimethicone | 3.0 g |
| Phenoxyethanol | Phenoxyethanol | 0.8 g |
| Syncrowax HRC | Tribehenin | 1.0 g |
| Crodamol STS | PPG 3 Benzyl Ether Myristate | 2.0 g |
| Prisorine 3758 | Hydrogenated polyisobutene | 19.0 g |
| H2O | Water | QS 100 g |
| PHASE C | | |
| Composition containing 0.05% by weight of peptide or peptidic compound according to the invention in an oily excipient | | 1.0 g (i.e. 5 ppm of peptide or peptidic compound) |
| PHASE D | | |
| Vanilla fragrance | Fragrance | 0.1 g |

Protocol:

Weigh Phase A, set to heat at 85° C. and mix. Slowly pour Phase A into Phase B, mixing. Add Phase C and homogenise. Add Phase D at around 35° C. and mix until cooled.

Properties:

The oil is particularly effective in moisturising the skin, particularly dry areas such as the hands and feet. It simultaneously firms and replumps the skin and makes it more soft and silky.

Example 3.4

Formulation of an Anti-Ageing Cream

| Composition | INCI Name | 100 g |
|---|---|---|
| PHASE A | | |
| H₂O | | qsp 100 g |
| Ultrez 10 | Carbomer | 0.15 g |
| PHASE B | | |
| Glycerine | Glycerin | 3.50 g |
| PART C | | |
| Volpo S 2 | Steareth 2 | 0.40 g |
| Crodafos CES | Cetearyl alcohol, dicetyl phosphate | 4.00 g |
| DC 345 | Cyclohexasiloxane | 2.00 g |
| Crodamol OSU | Dioctyl succinate | 7.00 g |

| Composition | INCI Name | 100 g |
|---|---|---|
| Volpo S 10 | Steareth 10 | 1.20 g |
| Nipastat | Mixed parabens | 0.30 g |
| PHASE D | | |
| Sorbate | Sorbate | 0.10 g |
| PHASE E | | |
| H2O | | 2.50 g |
| NaOH 38% | Sodium hydroxide | 0.30 g |
| PHASE F | | |
| Fragrance | Fragrance | 0.10 g |
| PHASE G | | |
| Pal-KMO2K-OH (0.05% by weight) in stabilised aqueous solution (water/glycerine/carbopol) | | 1.0 g (i.e. 5 ppm of peptide) |

Protocol:

The Ultrez 10 is dispersed in water until it thickens, following which Phase B is added and the mixture heated at 75° C. Phase C is heated separately at 75° C. The two phases are mixed and then homogenised and Phase D is added. The mixture is then neutralised with Phase E and cooled to 30° C. To finish, Phases F and G are added and the pH is adjusted to approximately 6 with NaOH.

Properties:

The emulsion obtained is suitable for old and/or fragile skin to improve its general state and particularly to improve wrinkles and fine lines, bags and dark circles, to treat dryness, reduce redness and irritation, improve suppleness and elasticity of the skin and to brighten the complexion.

Example 3.5

Formulation of an Anti-Ageing Cream

| Composition | INCI Name | 1 | 2 | 3 | 4 | 5 | 6 | 7 |
|---|---|---|---|---|---|---|---|---|
| PHASE A | | | | | | | | |
| H$_2$O | | qsp 100 g | qsp 100 g | qsp 100 g | qsp 100 g | qsp 100 g | qsp 100 g | qsp 100 g |
| Ultrez 10 | Carbomer | 0.15 g | 0.15 g | 0.15 g | 0.15 g | 0.15 g | 0.15 g | 0.15 g |
| PHASE B | | | | | | | | |
| Glycerine | Glycerin | 3.50 g | 3.50 g | 3.50 g | 3.50 g | 3.50 g | 3.50 g | 3.50 g |
| PART C | | | | | | | | |
| Volpo S 2 | Steareth 2 | 0.40 g | 0.40 g | 0.40 g | 0.40 g | 0.40 g | 0.40 g | 0.40 g |
| Crodafos CES | Cetearyl alcohol, dicetyl phosphate | 4.00 g | 4.00 g | 4.00 g | 4.00 g | 4.00 g | 4.00 g | 4.00 g |
| DC 345 | Cyclohexasiloxane | 2.00 g | 2.00 g | 2.00 g | 2.00 g | 2.00 g | 2.00 g | 2.00 g |
| Crodamol OSU | Dioctyl succinate | 7.00 g | 7.00 g | 7.00 g | 7.00 g | 7.00 g | 7.00 g | 7.00 g |
| Volpo S 10 | Steareth 10 | 1.20 g | 1.20 g | 1.20 g | 1.20 g | 1.20 g | 1.20 g | 1.20 g |
| Nipastat | Mixed parabens | 0.30 g | 0.30 g | 0.30 g | 0.30 g | 0.30 g | 0.30 g | 0.30 g |
| PHASE D | | | | | | | | |
| Sorbate | Sorbate | 0.10 g | 0.10 g | 0.10 g | 0.10 g | 0.10 g | 0.10 g | 0.10 g |
| PHASE E | | | | | | | | |
| H2O | | 2.50 g | 2.50 g | 2.50 g | 2.50 g | 2.50 g | 2.50 g | 2.50 g |
| NaOH 38% | Sodium hydroxide | 0.30 g | 0.30 g | 0.30 g | 0.30 g | 0.30 g | 0.30 g | 0.30 g |
| PHASE F | | | | | | | | |
| Fragrance | Fragrance | 0.10 g | 0.10 g | 0.10 g | 0.10 g | 0.10 g | 0.10 g | 0.10 g |
| PHASE G | | | | | | | | |
| Peptide* | | 1.0 g** | 1.0 g** | 1.0 g** | 1.0 g** | 1.0 g** | 1.0 g** | 1.0 g** |
| Niacinamid | | 0.3 g | — | — | — | — | — | — |
| Vit. E acetate | | — | 0.2 g | — | — | — | — | — |
| Retinol | | — | — | 0.1 g | — | — | — | — |
| Hexamidine | | — | — | — | 0.4 g | — | — | — |
| α-lipoic acid | | — | — | — | — | 0.5 g | — | — |
| DHEA | | — | — | — | — | — | 0.2 | — |
| Resveratrol | | — | — | — | — | — | — | 0.1 |

*Peptide or peptidic compound according to the invention (0.05% by weight) in stabilised aqueous solution (water/glycerine/carbopol)

**1.0 g (i.e. 5 ppm of peptide or peptidic compound)

Example 3.6

Formulation of an Anti-Dandruff Shampoo

| Composition | INCI Name | 100 g |
|---|---|---|
| PHASE A | | |
| H₂O | Water (aqua) | qsp 100 g |
| Citric acid | | 0.24 g |
| Tridosium citrate | | 1.20 g |
| Preservative | | qs |
| PHASE B | | |
| Empicol ESB3 | Sodium Laureth | 10.0 g |
| Crodasinic LS30 | Sodium Lauroyl Sulfate | 2.00 g |
| Incronam 30 | Sarcosinate | 5.00 g |
| Crothix Liquid | Cocamidopropyl Betaine, PEG-150, Pentaerythrityl Tetrastearate (and) PEG-6 Capryl/Capric Glycerides (and) Water | 5.00 g |
| PART C | | |
| Peptide or peptidic compound according to the invention (0.05% by weight) in a glycerine solution | | 1.0 g (i.e. 5 ppm of peptide or peptidic compound) |
| PHASE D | | |
| Fragrance | | 0.1 g |

Protocol:

Weigh Phase B, then melt and cool it. Add Phase A, mixing. Mix Phase C and add the A+B mixture, then add Phases C then D.

Properties:

The general condition of the hair is improved, it is stronger, softer, smoother and more shiny. The shampoo is effective by regular applications to combat dandruff, in particular through improved moisturisation of the scalp.

Example 3.7

Hair Loss Lotion

| Composition | INCI Name | 100 g |
|---|---|---|
| PHASE A | | |
| Incroquat Behenyl TMC | Behentrionium Chrloride (and) Cetearyl Alcohol | 3.00 g |
| Phenyl Trimethicone | | 1.00 g |
| Conservateurs | | 0.20 g |
| PHASE B | | |
| Potassium sorbate | Potassium Sorbate | 0.10 g |
| Demineralised water | Water (Aqua) | qsp 100 g |
| PART C | | |
| Apigenine | Apigenin | 0.0001 g |
| Peptide or peptidic compound according to the invention (0.05% by weight) in a glycerine solution | | 1.0 g (i.e. 5 ppm of peptide or peptidic compound) |

-continued

| Composition | INCI Name | 100 g |
|---|---|---|
| PHASE D | | |
| Fragrance | Fragrance | 0.10 g |
| Phase E | | |
| Demineralised water | Water (Aqua) | 0.25 g |
| Sarcolactic acid | | 0.025 g |

Protocol:

Heat Phase A to 85° C. Heat Phase B to 85° C. Pour Phase A into Phase B, mixing, homogenise well and cool to 35° C. Add Phase C and Phase D; adjust pH to ~5.5 with Phase E.

Properties:

This lotion delays hair loss, stimulates regrowth and improves the general condition of the hair follicles.

Example 3.8

Lightening Cream for the Face

| Composition | INCI Name | 100 g |
|---|---|---|
| PHASE A | | |
| Demineralised water | Water (aqua) | qsp 100 g |
| Ultrez 10 | Carbomer | 0.10 g |
| PHASE B | | |
| Transcutol | | 3.00 g |
| Glycerine | | 8.00 g |
| PART C | | |
| Potassium sorbate | Potassium Sorbate | 0.10 g |
| PHASE D | | |
| Volpo S2 | Steareth 2 | 0.60 g |
| Crodafos CES | Cetearyl Alcohol, Dicetyl Phosphate, Ceteth 10 Phosphate | 4.00 g |
| DC 344 | Cyclomethicone | 2.00 g |
| Crodamol GTCC | Caprylic/Capric triglyceride | 10.00 g |
| Crill 3 | Sorbitan Stearate | 1.60 g |
| Mixed Parabens | | 0.30 g |
| PHASE E | | |
| NaOH 30% | Sodium Hydroxide | 0.30 g |
| Demineralised water | Water (aqua) | 3.00 g |
| PHASE F | | |
| Kaempferol | | 0.00008 g |
| Peptide or peptidic compound according to the invention (0.05% by weight) in a solution of glycerine | | 2.0 g (i.e. 10 ppm of peptide or peptidic compound) |

Protocol:

The Ultrez 10 from Phase A is dispersed in water until it swells. Phase B and Phase C are then added and heated to 75°

C. Phase D is heated separately to 75° C. and mixed. Phase D is then poured into Phase (A+B+C), mixing. The mixture is homogenised and then neutralised with Phase E. The formulation is cooled to 35° C. and Phase F is then added.

Properties:

The cream leaves the skin more hydrated, suppler and more elastic and also lightens the skin of the face making the complexion brighter and more even.

Example 3.9

Slimming Cream

| Composition | INCI Name | 100 g |
|---|---|---|
| PHASE A | | |
| Demineralised water | Water (aqua) | qsp 100 g |
| Ultrez 10 | Carbomer | 0.40 g |
| PHASE B | | |
| Phenova | Phenoxyethanol (and) Crodarom Mixed Parabens | 0.80 g |
| Glycerine | | 5.00 g |
| PART C | | |
| Crodamol OP | Ethylhexyl palmitate | 4.00 g |
| Crodacol CS90 | Cetearyl alcohol | 0.50 g |
| Crodamol ML | Myristyl Lactate | 0.30 g |
| Crillet 1 | Polysorbate 20 | 1.00 g |
| PHASE D | | |
| Pemulen TR2 | Acrylates/C10-30 Alkyl Acrylate Crosspolymer | 0.20 g |
| DC 345 | Cyclomethicone | 2.00 g |
| PHASE E | | |
| Potassium sorbate | Potassium sorbate | 0.10 g |
| PHASE F | | |
| NaOH 38% | Sodium Hydroxide | 0.60 g |
| Demineralised water | Water (aqua) | 6.00 g |
| PHASE G | | |
| Galangin | *Ilex Paraguariensis* (Leaf) Extract - Aqua (water) - Butylene Glycol - *Coffea Arabica* (Coffee seed) Bean Extract - PEG-60 Almond Glycerides - Glycerin - Cetyl Hydroxyethylcelulose | 3.00 g |
| Unislim ® | | 3.00 g |
| Peptide or peptidic compound according to the invention (0.05% by weight) in a solution of glycerine | | 1.5 g (i.e. 10 ppm of peptide or peptidic compound) |

Protocol:

The Ultrez 10 from Phase A is dispersed in water until it swells. Phase B is mixed and heated to 60° C. until dissolved. Phase B is added to Phase A, mixing. Phase (A+B) is heated. Phase C is weighed and heated to 75° C. Phase C is then added to Phase (A+B), mixing. The mixture is homogenised carefully and Phase D is added. Phase E is added at approximately 50° C.; the mixture is then neutralised with Phase F. Phase G is added at approximately 35° C. and the pH adjusted to approximately 6.30.

Properties:

The emulsion has effective slimming action, particularly on cellulite. It refines the silhouette, redensifying the skin and making it softer and firmer.

It is obvious that the examples described above are provided only for illustrative purposes for the invention but are not restrictive. In particular many other examples of galenics can clearly be considered for the professional in the cosmetic field.

The invention claimed is:

1. A peptide of following formula I:

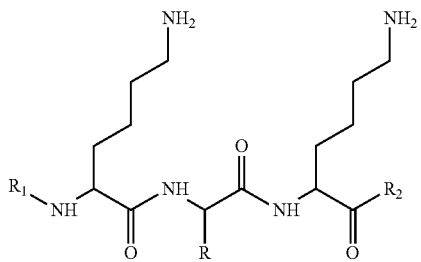

wherein R is a side chain of methionine having a di-oxidized sulfur group;
$R_1$ is either H or a lipophilic chain; and
$R_2$ is either OH or a lipophilic chain.

2. The peptide according to claim 1, wherein $R_1$ is an acyl or sulfonyl group selected from a biotinoyl group or a group having an alkyl, aryl, aralkyl, sugar or alkoxy 1 to 24 carbon atom chain, said chain being linear, branched or cyclic, saturated or unsaturated, hydroxylated or non-hydroxylated, sulfur-containing or non-sulfur-containing.

3. The peptide according to claim 1, wherein $R_2$ is a —O—$R_7$ group or a —$NR_8R_9$ group, $R_7$, $R_8$ and $R_9$ being independently from each other a hydrogen, an alkyl, aryl, aralkyl, acyl, sulfonyl, sugar or alkoxy of 1 to 24 carbon atoms chain, said chain being linear, branched or cyclic, saturated or unsaturated, hydroxylated or non-hydroxylated, sulfur-containing or non-sulfur-containing.

4. The peptide according to claim 1, wherein $R_1$ is a lipophilic chain and $R_2$ is OH.

5. The peptide according to claim 4, having the formula Pal-KMO$_2$K-OH, the methionine having a di-oxidized sulfur, wherein $R_1$ is palmitoyl and $R_2$ is OH.

6. A composition comprising the peptide of claim 1 and a physiologically acceptable medium.

7. The composition of claim 6 wherein said peptide is Pal-KMO$_2$K-OH.

8. The composition according to claim 6 further comprising a *Portulaca pilosa* plant extract, and wherein said extract is obtained using a method comprising a fatty ester.

9. The composition according to claim 6, wherein the proportion of peptide comprises between 0.00001% and 15% with regard to the total weight of the composition.

10. The composition of claim 9 wherein the proportion of peptide comprises between 0.001% and 5%.

11. A method to improve the general state of the skin and skin appendages comprising topically applying an effective amount of the composition of claim 6.

12. The method according to claim 11, wherein said improvement comprises treating intrinsic and extrinsic signs of skin aging selected from the group consisting of wrinkles, fine lines, discontinuities and roughness of the skin, skin sagging, skin spots and loss of brightness of complexion.

13. The method according to claim 11, wherein said improvement comprises improving mechanical properties of the skin selected from the group consisting of skin tonicity, skin firmness and skin elasticity.

14. The method according to claim 11 wherein said improvement comprises improving density of the dermis and epidermis, and giving or restoring volume to the dermis and epidermis.

15. The method according to claim 11 wherein said improvement comprises treating skin dehydration.

* * * * *